(12) United States Patent
Hammon et al.

(10) Patent No.: US 8,076,510 B2
(45) Date of Patent: Dec. 13, 2011

(54) PROCESS FOR STARTING-UP A HETEROGENEOUSLY CATALYZED PARTIAL GAS PHASE OXIDATION OF ACROLEIN TO ACRYLIC ACID OR OF METHACROLEIN TO METHACRYLIC ACID

(75) Inventors: Ulrich Hammon, Mannheim (DE); Thorsten Friese, Mannheim (DE); Jochen Petzoldt, Weisenheim am Berg (DE); Klaus Joachim Mueller-Engel, Stutensee (DE); Ulrich Cremer, Mannheim (DE); Andreas Raichle, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 685 days.

(21) Appl. No.: 12/107,420

(22) Filed: Apr. 22, 2008

(65) Prior Publication Data

US 2008/0269521 A1 Oct. 30, 2008

Related U.S. Application Data

(60) Provisional application No. 60/907,954, filed on Apr. 24, 2007.

(30) Foreign Application Priority Data

Apr. 24, 2007 (DE) .......................... 10 2007 019 597

(51) Int. Cl.
*C07C 51/16* (2006.01)
(52) U.S. Cl. ........................................ 562/545; 562/532
(58) Field of Classification Search .................. 562/545, 562/532
See application file for complete search history.

(56) References Cited

U.S. PATENT DOCUMENTS

| 5,739,391 | A | 4/1998 | Ruppel et al. |
| 6,582,667 | B1 | 6/2003 | Ogata et al. |
| 6,888,024 | B2 | 5/2005 | Dieterle et al. |
| 6,982,347 | B2 * | 1/2006 | Dieterle et al. ............... 562/535 |
| 7,119,227 | B2 | 10/2006 | Sakakura et al. |
| 7,144,557 | B2 | 12/2006 | Yada et al. |
| 7,157,597 | B2 | 1/2007 | Dieterle et al. |
| 7,164,039 | B2 | 1/2007 | Petzoldt et al. |
| 7,297,814 | B2 | 11/2007 | Yada et al. |
| 7,439,389 | B2 | 10/2008 | Dieterle et al. |
| 2004/0015012 | A1 | 1/2004 | Hammon et al. |
| 2004/0249000 | A1 | 12/2004 | Yada et al. |
| 2004/0250868 | A1 | 12/2004 | Yada et al. |
| 2005/0096483 | A1 | 5/2005 | Dieterle et al. |
| 2005/0261517 | A1 | 11/2005 | Dieterle et al. |
| 2007/0021631 | A1 | 1/2007 | Yada et al. |
| 2007/0021632 | A1 | 1/2007 | Yada et al. |
| 2007/0167648 | A1 | 7/2007 | Cremer et al. |

(Continued)

FOREIGN PATENT DOCUMENTS

DE 44 31 949 A1 3/1995

(Continued)

*Primary Examiner* — Victor Oh
(74) *Attorney, Agent, or Firm* — Oblon, Spivak, McClelland, Maier & Neustadt, L.L.P.

(57) ABSTRACT

A process for starting-up a heterogeneously catalyzed partial gas phase oxidation of acrolein to acrylic acid or of methacrolein to methacrylic acid over a fixed catalyst bed disposed in a tube bundle reactor cooled by a heat exchange medium, wherein the temperature of the heat exchange medium is $\geq 290°$ C. and the temperature of that reactor plate surface which faces the reaction gas entry mixture and the temperature of the reaction gas entry mixture itself are $\leq 285°$ C.

16 Claims, 3 Drawing Sheets

U.S. PATENT DOCUMENTS

Figure 1:
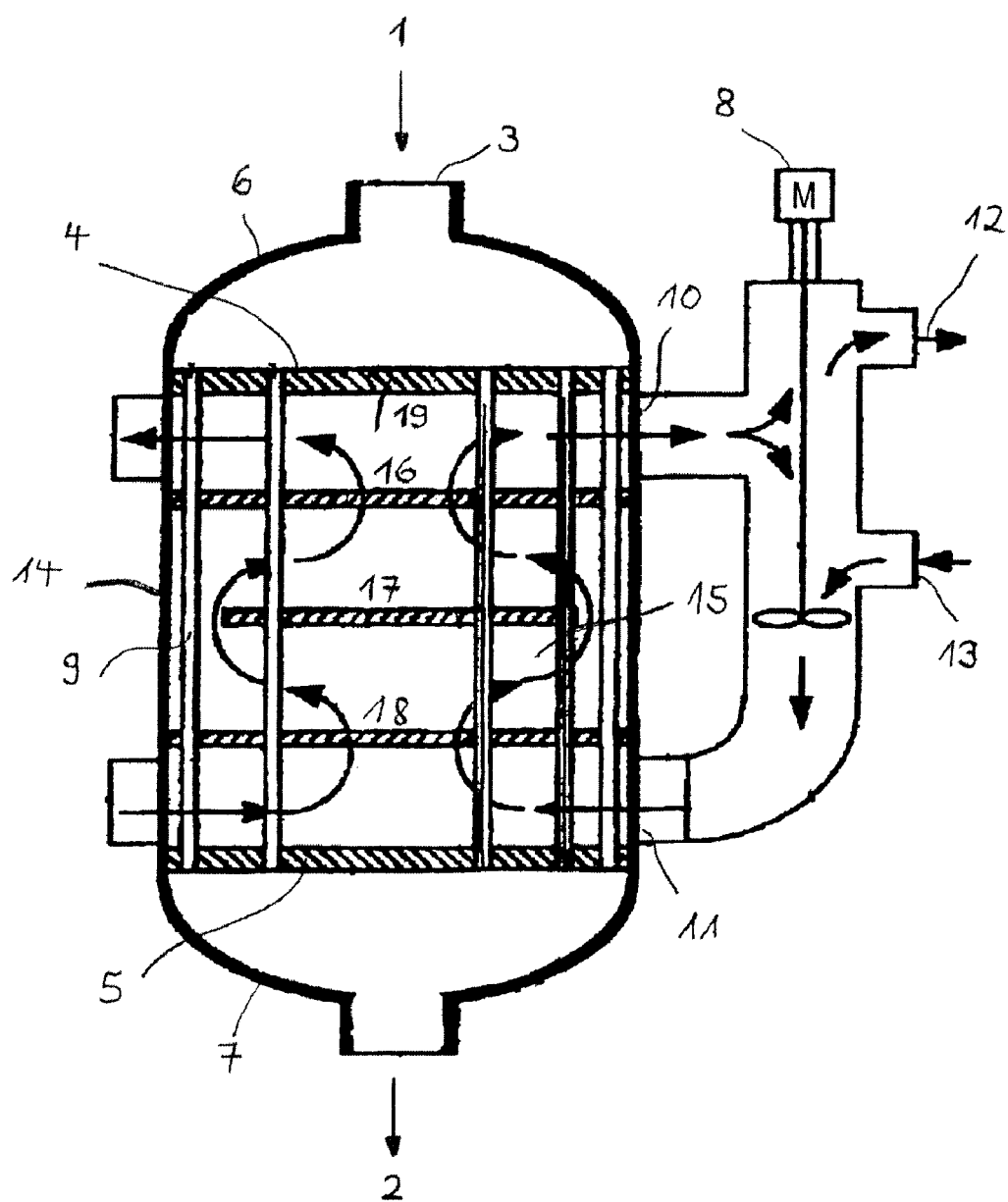

| | | |
|---|---|---|
| 2008/0187467 A1 | 8/2008 | Dieterle et al. |
| 2008/0216915 A1 | 9/2008 | Yada et al. |
| 2008/0234522 A1 | 9/2008 | Yada et al. |
| 2008/0253943 A1 | 10/2008 | Yoda et al. |
| 2008/0260605 A1 | 10/2008 | Dieterle et al. |

FOREIGN PATENT DOCUMENTS

| | | |
|---|---|---|
| DE | 103 13 208 A1 | 10/2004 |
| DE | 103 13 211 A1 | 10/2004 |
| DE | 103 13 213 A1 | 10/2004 |
| DE | 103 13 214 A1 | 10/2004 |
| DE | 10 2004 025 445 A1 | 2/2005 |
| DE | 699 15 952 T2 | 2/2005 |
| DE | 103 50 822 A1 | 6/2005 |
| EP | 0 700 893 A1 | 3/1996 |
| EP | 1 658 893 A1 | 5/2006 |
| EP | 1 695 954 A1 | 8/2006 |
| EP | 1 734 030 A1 | 12/2006 |
| WO | WO 03/055835 A1 | 7/2003 |
| WO | WO 03/057653 A1 | 7/2003 |
| WO | WO 03/059857 A1 | 7/2003 |
| WO | WO 03/076373 A1 | 9/2003 |
| WO | WO 2006/092410 A1 | 9/2006 |

* cited by examiner

US 8,076,510 B2

PROCESS FOR STARTING-UP A HETEROGENEOUSLY CATALYZED PARTIAL GAS PHASE OXIDATION OF ACROLEIN TO ACRYLIC ACID OR OF METHACROLEIN TO METHACRYLIC ACID

The present invention relates to a process for starting-up a heterogeneously catalyzed partial gas phase oxidation of acrolein to acrylic acid or of methacrolein to methacrylic acid in a fixed catalyst bed which is disposed in a tube bundle reactor in the reaction tubes of a vertical bundle of reaction tubes surrounded by a reactor jacket, both ends of the individual reaction tubes being open and the upper end of each reaction tube ending sealed into a passage orifice of an upper tube plate sealed at the top into the reactor jacket and the lower end ending sealed into a passage orifice of a lower tube plate sealed at the bottom into the reactor jacket, the exterior of the reaction tubes, the upper and the lower tube plate and the reactor jacket together delimiting the reaction tube surrounding space, and each of the two tube plates being spanned by a reactor hood having at least one orifice, in which, in order to begin the startup, a reaction gas entry mixture comprising $\geq 3\%$ by volume of acrolein or methacrolein and also molecular oxygen is fed to the reaction tubes of the tube bundle reactor via the at least one orifice, referred to hereinafter as E, in one of the two reactor hoods, and the product gas mixture which results through partial gas phase oxidation of acrolein or methacrolein to acrylic acid or methacrylic acid in the course of passage through the fixed catalyst bed disposed in the reaction tubes and comprises acrylic acid or methacrylic acid is removed via the at least one orifice of the other reactor hood, while, on the jacket side of the tube bundle reactor, at least one liquid heat exchange medium is conducted around the reaction tubes such that each of the two surfaces of the two tube plates facing one another are wetted by liquid heat exchange medium and the at least one liquid heat exchange medium is conducted into the reaction tube surrounding space with the temperature $T_H^{in}$ and is conducted out of the reaction tube surrounding space again with the temperature $T_H^{out}$.

Acrylic acid and methacrylic acid are reactive monomers which are suitable as such or in the form of their alkyl esters, for example, for preparing polymers which can find uses including as adhesives or water-absorbing materials (for example for use in the hygiene sector).

It is known that acrylic acid and methacrylic acid can be prepared on the industrial scale by heterogeneously catalyzed partial gas phase oxidation of their precursor compounds acrolein and methacrolein, the fixed catalyst bed being disposed in the reaction tubes of a tube bundle reactor as described at the outset, while, on the jacket side of the tube bundle reactor, at least one liquid heat exchange medium is conducted around the reaction tubes such that each of the two surfaces of the two tube plates facing one another is wetted by a liquid heat exchange medium (cf., for example, EP-A 700893, DE-A 4 431 949, WO 03/057653, EP-A 1695954, WO 03/055835, WO 03/059857, WO 03/076373 and DE 699 15952 T2).

In general, the components of the tube bundle reactor are manufactured from steel. Use for manufacturing steel is both stainless steel (for example of DIN materials number 1.4541 or material 1.4571 (to DIN EN 10020)) and black steel or ferritic steel (for example DIN materials 1.0481, 1.0315 or material 1.0425 (to DIN EN 10020)). Frequently, all components of the tube bundle reactor are manufactured from the same steel type.

The space delimited by the exterior of the reaction tubes, the two tube plates and the reactor jacket together, within which the liquid heat exchange medium is conducted, shall be referred to in this document as the reaction tube surrounding space. In the simplest manner, only one liquid heat exchange medium is conducted within the reaction tube surrounding space (referred to hereinafter as a one-zone mode in the one-zone tube bundle reactor).

The liquid heat exchange medium is conducted to the reaction tube surrounding space typically at its upper or at its lower end with an entrance temperature $T_H^{in}$ through orifices in the reactor jacket, and conducted back out of the reaction tube surrounding space at the opposite end with an exit temperature $T_H^{out}$ through orifices in the reactor jacket.

As a result of the exothermicity of the gas phase partial oxidation, during the performance of the partial oxidation, $T_H^{out} > T_H^{in}$. With the aid of a heat exchanger, heat is withdrawn from a portion or the entirety of the liquid heat exchange medium conducted out of the reaction tube surrounding space before it is fed back to the reaction tube surrounding space with the temperature $T_H^{in}$. In the reaction tube surrounding space, the liquid heat exchange medium can in principle be conducted around the reaction tubes in simple cocurrent or countercurrent to the reaction gas mixture flowing into the reaction tube. However, it can also be conducted around the reaction tubes in a meandering manner with the aid of corresponding deflecting disks, such that a cocurrent or countercurrent to the flow direction of the reaction gas mixture in the reaction tubes exists merely over the entire reaction tube surrounding space.

The heat exchange medium has to be liquid under the use conditions, i.e., appropriately from an application point of view, has a melting point in the range from 50 to 250° C., preferably from 150 to 200° C.

Useful such liquid heat exchange media include, for example, melts of salts such as potassium nitrate, potassium nitrite, sodium nitrite and/or sodium nitrate, and also melts of metals such as sodium, mercury and alloys of different metals. However, it is also possible to use ionic liquids or heat carrier oils.

The composition of the reaction gas entry mixture, the loading of the fixed catalyst bed disposed in the reaction tubes with acrolein or methacrolein, the entry point of the heat exchange medium into the reaction tube surrounding space, $T_H^{in}$, the volume flow rate of the heat exchange medium, the fixed catalyst bed and the other reaction conditions are generally selected such that the conversion of acrolein based on a single throughput of the reaction gas mixture through the reaction tubes is $\geq 90$ mol %, in many cases $\geq 95$ mol %, preferably $\geq 98$ mol %, and the selectivity of the accompanying acrylic acid formation is $\geq 90$ mol % (or the conversion of methacrolein based on a single throughput of the reaction gas mixture through the reaction tubes is $\geq 50$ mol %, in many cases $\geq 60$ mol %, and in some cases $\geq 70$ mol %, and the selectivity of the accompanying methacrylic acid formation is $\geq 70$ mol %, advantageously $\geq 80$ mol %). The difference $T_H^{out} - T_H^{in}$ is generally kept at from >0 to 10° C., frequently from 2 to 8° C., in many cases from 3 to 6° C.

To improve the selectivity of target product formation, the heterogeneously catalyzed partial gas phase oxidation of acrolein to acrylic acid or of methacrolein to methacrylic acid can also be performed as a multizone method (for example two-zone method) in a multizone tube bundle reactor (for example in a two-zone tube bundle reactor).

In this case, a plurality of (for example two) liquid heat exchange media essentially spatially separated from one another (which are normally of the same type) are conducted within the reaction tube surrounding space (these may, for example, be separated by separating tube plates which are inserted into the reaction tube surrounding space and have appropriate passage orifices for the reaction tubes).

The reaction tube longitudinal section over which the particular liquid heat exchange medium extends represents one temperature or reaction zone (the one-zone tube bundle reactor correspondingly has only one reaction zone). Within the particular temperature zone, the liquid heat exchange medium can be conducted as in the one-zone method (also relative to the flow direction of the reaction gas mixture). For the difference between $T_H^{out}$ and $T_H^{in}$, the statements made for the one-zone method regarding the individual temperature zone apply in an essentially identical manner.

Figure 2:
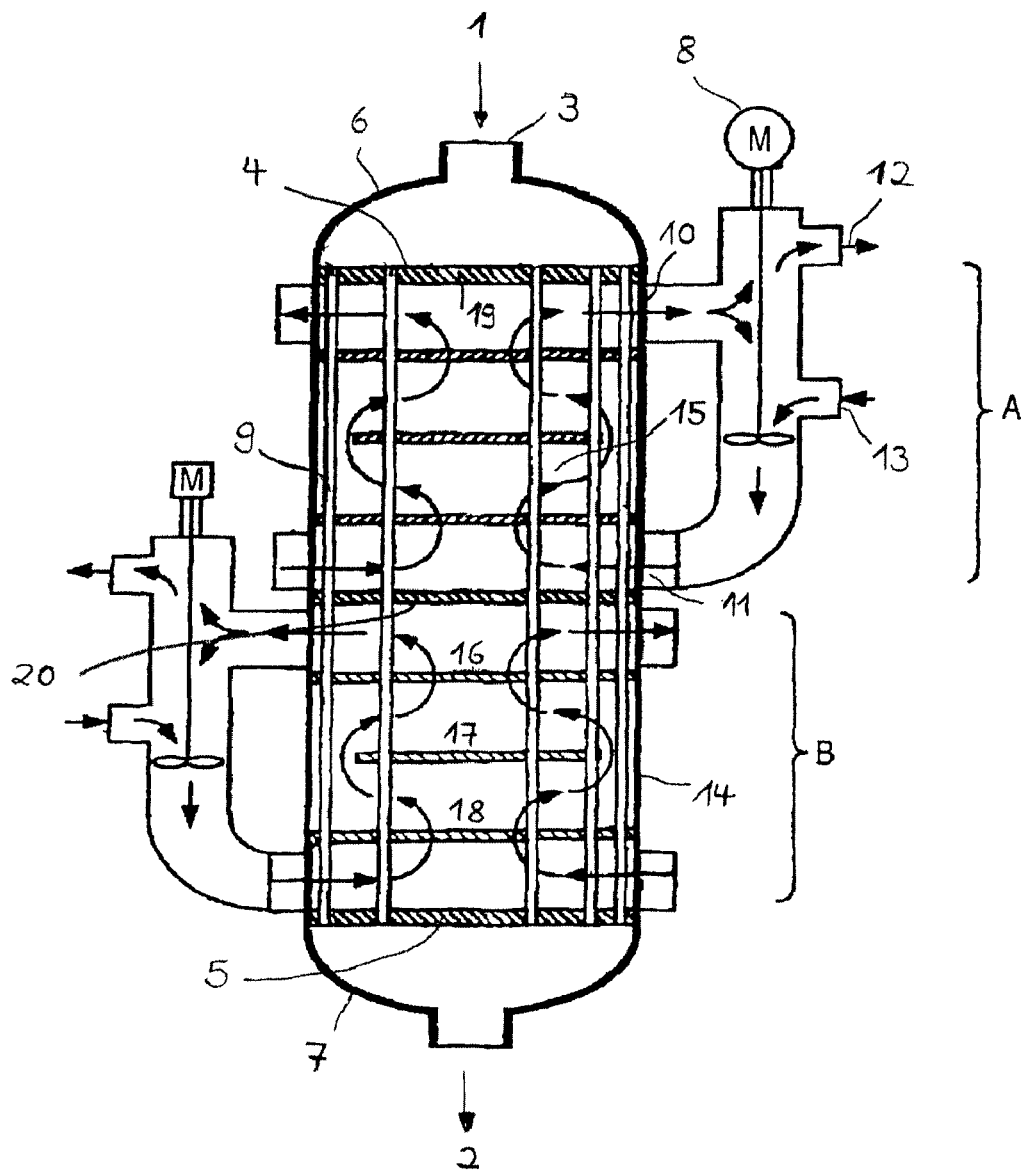
Figure 3:
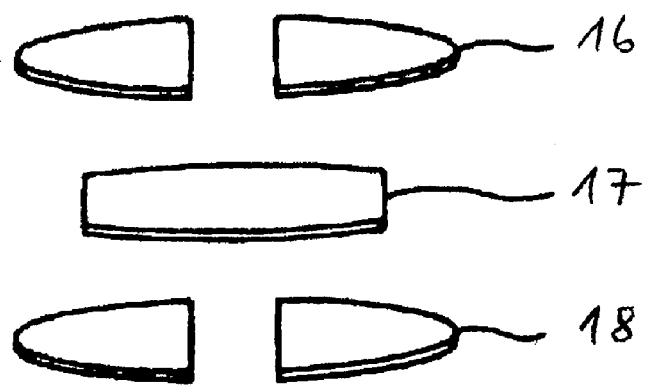
Figure 4:
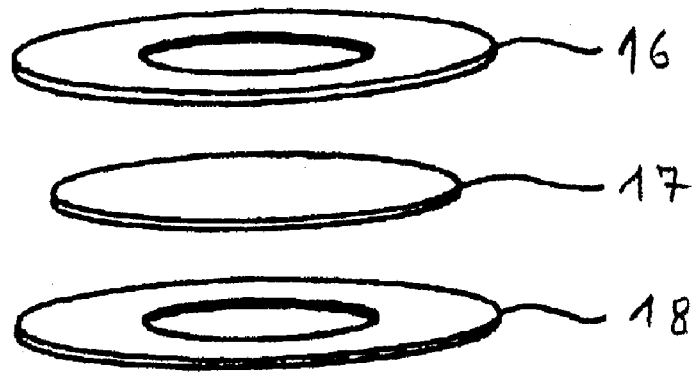

A graphic distinction between a one-zone and a two-zone method (between a one-zone tube bundle reactor and a two-zone tube bundle reactor) is shown schematically and by way of example by FIGS. 1 and 2 of this document. FIGS. 3 and 4 show examples for the configuration of the deflecting disks (they typically comprise passage orifices for the reaction tubes).

Multizone methods are, for example, described in documents EP-A 1734030, DE-A 10313214, DE-A 10313213, DE-A 10313211, DE-A 10313208 and in the prior art cited in these documents. They are advantageous in particular when a high acrolein or methacrolein loading of the fixed catalyst bed is selected. The loading of the fixed catalyst bed with reaction gas mixture or with one reaction gas mixture component is understood to mean the amount of reaction gas mixture or reaction gas mixture component in standard liters (I (STP); of the volume that the corresponding amount would take up theoretically in gaseous form at 0° C. and 1 atm) which is conducted through one liter of fixed catalyst bed (pure inert material beds are not included) per hour.

The reaction gas entry mixture itself may, in the different procedures, be conducted either from the top downward or from the bottom upward in the reaction tubes in the tube bundle reactor (i.e. the at least one orifice E may be disposed either in the upper or in the lower reactor hood). The same applies to the conduction of the liquid heat exchange medium.

The target product is removed from the product gas mixture obtained in a heterogeneously catalyzed partial gas phase oxidation of acrolein to acrylic acid or of methacrolein to methacrylic acid generally using thermal separating processes. To this end, the target product is normally first converted to the condensed phase by condensative and/or absoptive measures. It is subsequently removed therefrom as a pure product typically using extractive, rectificative and/or crystallizative measures. These are performed, inter alia, in separating columns comprising separating internals (for example random packings, structured packings and/or trays).

It is known from the prior art that the heterogeneously catalyzed partial gas phase oxidation of acrolein to acrylic acid or of methacrolein to methacrylic acid over the freshly charged fixed catalyst bed can be performed generally at temperatures of the at least one liquid heat exchange medium which are such that, where the liquid heat exchange medium wets the tube plate (also referred to later in this document as reactor plate E) spanned by the reactor hood having at least one orifice E (also referred to later in this document as reactor hood E), the temperature of the liquid heat exchange medium is less than 290° C. (referred to hereinafter in this document as wetting temperature E ($T_H^E$); it may either be a $T_H^{in}$ or a $T_H^{out}$).

The temperature of the reaction gas entry mixture on entry into the at least one orifice E (referred to hereinafter as $T_G^E$), according to the statements in the prior art, can in principle be below the wetting temperature E ($T_H^E$). This is possible by virtue of the fact that the reaction tubes, in flow direction of the reaction gas mixture, are normally charged first with a longitudinal section of shaped bodies which are inert with respect to the partial oxidation before the catalytically active section of the fixed catalyst bed with shaped bodies having catalytically active composition begins. In the course of flow through this inert section, the reaction gas entry mixture can then be heated to the temperature of the heat exchange medium which flows around the corresponding catalytically active reaction tube section.

It will be appreciated that the reaction gas entry mixture, on entry into the at least one orifice E (reaction gas entry mixture is generally fed only through one orifice E and product gas removed only via one orifice in the other reactor hood; in principle, it is, though, also possible in each case to employ 2 or 3 or more such orifices in the particular reactor hood for this purpose), may, though, already be preheated to the value of the temperature $T_H^E$ which corresponds essentially to the initial reaction temperature. This is the temperature at which the catalyzed partial oxidation over the fixed catalyst bed disposed in the reaction tube begins. Since the heterogeneously catalyzed partial gas oxidation of acrolein to acrylic acid or of methacrolein to methacrylic acid is a markedly exothermic reaction, the temperature of the reaction gas mixture in the course of reactive passage through the fixed catalyst bed is otherwise normally different from the temperature of the liquid heat exchange medium which flows around the fixed catalyst bed outside the catalyst tubes. It is typically above the entrance temperature of the heat exchange medium $T_H^{in}$ into the corresponding reaction zone (temperature zone) and generally passes through an absolute maximum (hotspot maximum) along a reaction zone, or declines proceeding from such an absolute maximum value (if appropriate via further relative maxima).

It is also known from the prior art that a heterogeneously catalyzed partial gas phase oxidation of acrolein to acrylic acid or of methacrolein to methacrylic acid can be performed over one and the same fixed catalyst bed over a prolonged period. Typical operating times are 1 year and more.

However, a disadvantage of such a long-term operation over one and the same fixed catalyst bed is that, in spite of intermediately employed measures for its regeneration (cf., for example, DE-A 10350822), an increasing irreversible reduction in the quality of the fixed catalyst bed occurs from a certain operating time with increasing operating duration (cf., for example, DE-A 102004025445).

This increasing exhaustion of the quality of the fixed catalyst bed in the catalyst tubes which accompanies increasing operating time can, at least for a certain operating time, be counteracted by gradually increasing the entrance temperature of the at least one liquid heat exchange medium $T_H^{in}$ into the reaction tube surrounding space. This increase is necessarily also accompanied by an increase in $T_H^E$ which, with increasing operating time, leads to the temperature of the at least one liquid heat exchange medium, where it wets the reactor plate E, being 290° C. and more. For the overwhelming majority of catalysts suitable for a heterogeneously catalyzed partial gas phase oxidation of acrolein to acrylic acid or methacrolein to methacrylic acid, the partial oxidation process can still be operated with fully satisfactory conversions and target product selectivities even at $T_H^{in}$ values of up to 350° C. (for example 300° C., or 310° C., or 320° C., or 330° C., or 340° C.) and more (for example 360° C., or 370° C., or 380° C., or 390° C., or 400° C.). $T_H^{in}$ values above 400° C. will, however, usually be exceptional.

The increase of $T_H^{in}$, according to the prior art procedure (cf., for example, DE-A 10350822), is not normally accompanied by a simultaneous increase of $T_G^E$ of the reaction gas entry mixture. Instead, $T_G^E$ is normally left at the value with which the reaction gas entry mixture has been supplied to the tube bundle reactor during the performance of the partial oxidation over the freshly charged fixed catalyst bed.

Since this $T_G^E$ has a value below 290° C., the temperature of the surface of the reactor plate E facing toward the reactor hood having the orifice E is also below 290° C. in normal operation of the heterogeneously catalyzed gas phase partial oxidation (even when the $T_H^{in}$ of that heat exchange medium which wets the reactor plate E is $\geqq$290° C.), since this reactor plate surface is cooled continuously in continuous operation by the reaction gas entry mixture (which flows generally in a flow rate of at least 1000 m³ (STP)/(h·m²), frequently of at least 1500 m³ (STP)/(h·m²) or of at least 2500 m³ (STP)/(h·m²) onto the cross-sectional area of the reactor plate E).

However, the above is no longer the case when the heterogeneously catalyzed partial gas phase oxidation has to be interrupted. One possible type of reasons for interruption includes, for example, all possible operational disruptions detailed in the documents EP-A 1658893 and US-A 2004/00015012.

However, the reason for the interruption may also be that, in the course of the removal of the acrylic acid or methacrylic acid target products in the columns which comprise separating internals and are used for this purpose, undesired polymer formation occurs (both acrylic acid and methacrylic acid have a marked tendency to undesired free-radical polymerization). In order to be able to remove it, the partial oxidation process is, appropriately from an application point of view, interrupted.

In various cases, the interruption of the partial oxidation is also accompanied by a reduction in the entrance temperature of the at least one liquid heat exchange medium $T_H^{in}$ in order to save energy during the downtime.

In many cases, however, the temperature with which the at least one liquid heat exchange medium $T_H^{in}$ is fed to the reaction tube surrounding space is essentially retained during the interruption of the partial oxidation in order to maintain immediate operation readiness. At the same time, during the interruption of the partial oxidation, either no gas stream at all or at most a gas stream significantly lower (generally less than one third, frequently less than one fifth of the reaction gas entry mixture stream) compared to the reaction gas entry mixture stream is conducted through the tube bundle reactor via the at least one orifice E.

Once the applicant in these cases has subsequently restarted the partial oxidation, immediate shutdowns of the partial oxidation have frequently been triggered shortly thereafter, caused by a rapid rise in the temperature in the gas space of the reactor hood E. Protracted investigations and analyses of these facts showed that, in the case of the above-described variants of partial oxidation interruptions, compared to the situation in the case of regular operation of the partial oxidation, there is generally heating of that surface of the reactor plate E which faces that reactor hood which has the orifice E (referred to hereinafter in this document as reactor plate surface E) in the course of the interruption.

When, however, reaction gas entry mixture comprising $\geqq$3% by volume of acrolein or methacrolein, in the course of restart of the heterogeneously catalyzed partial gas phase oxidation, flows toward such a comparatively hot reactor plate surface E, this can trigger (with increasing probability with increasing temperature of the reactor plate surface E) a (thermal) exothermic homogeneous free-radical oxidation of the acrolein or methacrolein which can spread in the opposite direction to the flow direction of the reaction gas entry mixture (and comprise a thermal decomposition of the acrolein or methacrolein). At least one thermocouple projecting into the reactor hood E for safety reasons (when, for example, operational disruptions occur in the removal of heat of reaction of the regular heterogeneously catalyzed partial gas phase oxidation, it can get out of control and has to be stopped by an immediate shutdown (ending of the reaction gas mixture entry stream according to EP-A 1658893 or according to US 2004/00015012)) detects the heat of reaction released with the exothermic free-radical oxidation and hence triggers an immediate shutdown.

In the reaction tubes charged with shaped catalyst bodies and/or shaped inert bodies, such a thermal exothermic homogeneous free-radical oxidation of the acrolein or methacrolein, even at $T_H^E$ temperatures of $\geqq$290° C., essentially does not occur, since the large specific surface area of the shaped catalyst bodies and/or shaped inert bodies normally scavenges free radicals which form and hence normally extinguishes the free-radical chain reaction. Therefore, spreading of the thermal homogeneous free-radical oxidation (including decomposition) normally does not extend into the reaction tubes charged with the fixed catalyst bed.

It was therefore an object of the present invention to provide a process for starting-up a heterogeneously catalyzed partial gas phase oxidation of acrolein to acrylic acid or of methacrolein to methacrylic acid over a fixed catalyst bed disposed in the reaction tubes of a tube bundle reactor, which at least reduces or entirely prevents the above-described immediate shutdowns.

Accordingly, a process has been found for starting-up a heterogeneously catalyzed partial gas phase oxidation of acrolein to acrylic acid or of methacrolein to methacrylic acid in a fixed catalyst bed which is disposed in a tube bundle reactor in the reaction tubes of a vertical bundle of reaction tubes surrounded by a reactor jacket, both ends of the individual reaction tubes being open and the upper end of each reaction tube ending sealed into a passage orifice of an upper tube plate sealed at the top into the reactor jacket and the lower end ending sealed into a passage orifice of a lower tube plate sealed at the bottom into the reactor jacket, the exterior of the reaction tubes, the upper and the lower reactor plate and the reactor jacket together delimiting the reaction tube surrounding space, and each of the two tube plates being spanned by a reactor hood having at least one orifice, in which, in order to begin the startup, a reaction gas entry mixture comprising $\geqq$3% by volume of acrolein or methacrolein and also molecular oxygen is fed to the reaction tubes of the tube bundle reactor via the at least one orifice, referred to hereinafter as E, in one of the two reactor hoods, and the product gas mixture which results through partial gas phase oxidation of acrolein or methacrolein to acrylic acid or methacrylic acid in the course of passage through the fixed catalyst bed disposed in the reaction tubes and comprises acrylic acid or methacrylic acid is removed via the at least one orifice of the other reactor hood, while, on the jacket side of the tube bundle reactor, at least one liquid heat exchange medium is conducted around the reaction tubes such that each of the two surfaces of the two tube plates facing one another are wetted by liquid heat exchange medium and the at least one liquid heat exchange medium is conducted into the reaction tube surrounding space with the temperature $T_H^{in}$ and is conducted out of the reaction tube surrounding space again with the temperature $T_H^{out}$, wherein, at the time at which, in order to begin the startup, the reaction gas entry mixture comprising $\geqq$3% by volume of acrolein or methacrolein enters the reactor hood through the at least one orifice E, the temperature $T_H^{in}$ of the at least one liquid heat exchange medium which wets the tube plate spanned by the reactor hood having the at least one orifice E, referred to hereinafter as reactor plate E, is at least 290° C., the reaction gas entry mixture which enters the at least one orifice E (on entry into the at least one orifice E) has a temperature of ≦285° C., and the temperature of the surface of the reactor plate E facing the reactor hood having the at least one orifice E, referred to hereinafter as reactor plate surface E, has a value of ≦285° C.

The temperature $T_H^{in}$ of the at least one liquid heat exchange medium (useful liquid heat exchange media for the process according to the invention are all of those named at the outset of this document) which wets the reactor plate E (this temperature is also referred to in this document as $T_H^{in,E}$) may, in the course of the inventive startup, also be ≧291° C., or ≧292° C., or ≧293° C., or ≧294° C., or ≧295° C., or ≧296° C., or ≧297° C., or ≧298° C., or ≧299° C., or ≧300° C., or ≧301° C., or ≧302° C., or ≧303° C., or ≧304° C. It will be appreciated that $T_H^{in,E}$ in the process according to the invention may also be ≧305° C., or ≧310° C., or ≧315° C., or ≧320° C. Even $T_H^{in,E}$ values of ≧330° C. and ≧340° C. are possible in the process according to the invention, especially when it is a heterogeneously catalyzed partial oxidation of methacrolein to methacrylic acid. In general, $T_H^{in,E}$ will, however, be ≦400° C., frequently ≦375° C. and in many cases ≦350° C. It will be appreciated that, in an inventive startup, every single one of the aforementioned "≧relations" is also possible for $T_H^E$. It will be appreciated that, in an inventive startup, $T_H^{in,E}$ and $T_H^E$ may simultaneously each correspond to a single one of the aforementioned "≧relations".

The temperature of the reaction gas entry mixture on entry into the orifice E, i.e. $T_G^E$, may, in the inventive startup with all $T_H^{in,E}$ and $T_H^E$ values specified individually in this document, be ≦285° C., or ≦280° C., or ≦275° C., or ≦270° C., or ≦260° C., or ≦250° C., or ≦240° C., or ≦220° C., or ≦210° C., or ≦200° C. Typically, $T_G^E$ in the inventive startup will, however, be above (preferably at least 5° C. above) the dew point of the reaction gas entry mixture. That is the temperature at which there are manifestations of condensation (formation of liquid droplets) with the selected composition of the reaction gas entry mixture and at the selected working pressure in the reaction gas entry mixture within the reaction gas entry mixture. However, a reaction gas entry mixture comprising liquid droplets is capable of damaging the fixed catalyst bed as it flows through. Low values for $T_G^E$ are generally advantageous. This is especially true when the reaction tubes, in flow direction of the reaction gas entry mixture, first have a bed of shaped inert bodies. The length of such an inert bed may take up to 10%, or up to 20%, or up to 30% of the reaction tube length. In general, it will not be below 5% of this length. $T_G^E$ is preferably from 200 to 260° C. Especially when the partial oxidation of acrolein to acrylic acid or of methacrolein to methacrylic acid is not coupled to a preceding partial oxidation of the corresponding olefin to acrolein or methacrolein, $T_G^E$ may also be from 90 to 150° C.

It is also favorable in accordance with the invention in the inventive startup when the temperature of the surface E facing the reactor hood having the at least one orifice E, i.e. the reactor plate surface E, is ≦280° C., preferably ≦275° C., advantageously ≦270° C., especially advantageously ≦265° C., very especially advantageously ≦260° C., especially preferably ≦255° C., very especially preferably ≦250° C., or ≦245° C., or ≦240° C., particularly favorably ≦235° C., or ≦230° C., or ≦225° C., or ≦220° C., or ≦215° C., or ≦0° C., or ≦205° C., or ≦200° C. This temperature of the reactor plate surface E is also referred to in this document as $T_B^E$. Since the temperature of the reactor plate surface E over the surface E need not necessarily be homogeneous in all operating states (the surface temperatures in the center and at the periphery of the reactor plate accessible to the reaction gas are generally slightly elevated), $T_B^E$ in this document shall in particular be the higher of the two temperatures found in a temperature measurement at the aforementioned periphery (at the outermost reaction tube circle) and in the center of the tube plate.

Startups advantageous in accordance with the invention are thus, for example, those for which, simultaneously:

$T_H^{in,E}$ (and if appropriate $T_W^E$) is ≧290° C., $T_G^E$ is ≦285° C., $T_B^E$ is ≦280° C.; or $T_H^{in,E}$ (and if appropriate $T_W^E$) is ≧290° C., $T_G^E$ is ≦285° C., $T_B^E$ is ≦275° C.; or $T_H^{in,E}$ (and if appropriate $T_W^E$) is ≧290° C., $T_G^E$ is ≦285° C., $T_B^E$ is ≦260° C.; or $T_H^{in,E}$ (and if appropriate $T_W^E$) is ≧290° C., $T_G^E$ is ≦285° C., $T_B^E$ is ≦255° C.; or $T_H^{in,E}$ (and if appropriate $T_W^E$) is ≧290° C., $T_G^E$ is ≦285° C., $T_B^E$ is ≦250° C.; or $T_H^{in,E}$ (and if appropriate $T_W^E$) is ≧290° C., $T_G^E$ is ≦285° C., $T_B^E$ is ≦245° C.; or $T_H^{in,E}$ (and if appropriate $T_W^E$) is ≧290° C., $T_G^E$ is ≦285° C., $T_B^E$ is ≦240° C.; or $T_H^{in,E}$ (and if appropriate $T_W^E$) is ≧290° C., $T_G^E$ is ≦285° C., $T_B^E$ is ≦235° C.; or $T_H^{in,E}$ (and if appropriate $T_W^E$) is ≧290° C., $T_G^E$ is ≦285° C., $T_B^E$ is ≦230° C.; or $T_H^{in,E}$ (and if appropriate $T_W^E$) is ≧290° C., $T_G^E$ is ≦285° C., $T_B^E$ is ≦225° C.; or $T_H^{in,E}$ (and if appropriate $T_W^E$) is ≧290° C., $T_G^E$ is ≦280° C., $T_B^E$ is ≦280° C.; or $T_H^{in,E}$ (and if appropriate $T_W^E$) is ≧290° C., $T_G^E$ is ≦275° C., $T_B^E$ is ≦280° C.; or $T_H^{in,E}$ (and if appropriate $T_W^E$) is ≧290° C., $T_G^E$ is ≦270° C., $T_B^E$ is ≦280° C.; or $T_H^{in,E}$ (and if appropriate $T_W^E$) is ≧290° C., $T_G^E$ is ≦265° C., $T_B^E$ is ≦280° C.; or $T_H^{in,E}$ (and if appropriate $T_W^E$) is ≧290° C., $T_G^E$ is ≦260° C., $T_B^E$ is ≦280° C.; or $T_H^{in,E}$ (and if appropriate $T_W^E$) is ≧290° C., $T_G^E$ is ≦280° C., $T_B^E$ is ≦275° C.; or $T_H^{in,E}$ (and if appropriate $T_W^E$) is ≧290° C., $T_G^E$ is ≦280° C., $T_B^E$ is ≦270° C.; or $T_H^{in,E}$ (and if appropriate $T_W^E$) is ≧290° C., $T_G^E$ is ≦280° C., $T_B^E$ is ≦265° C.; or $T_H^{in,E}$ (and if appropriate $T_W^E$) is ≧290° C., $T_G^E$ is ≦280° C., $T_B^E$ is ≦260° C.; or $T_H^{in,E}$ (and if appropriate $T_W^E$) is ≧290° C., $T_G^E$ is ≦275° C., $T_B^E$ is ≦275° C.; or $T_H^{in,E}$ (and if appropriate $T_W^E$) is ≧290° C., $T_G^E$ is ≦275° C., $T_B^E$ is ≦270° C.; or $T_H^{in,E}$ (and if appropriate $T_W^E$) is ≧290° C., $T_G^E$ is ≦275° C., $T_B^E$ is ≦265° C.; or $T_H^{in,E}$ (and if appropriate $T_W^E$) is ≧290° C., $T_G^E$ is ≦275° C., $T_B^E$ is ≦260° C.; or $T_H^{in,E}$ (and if appropriate $T_W^E$) is ≧290° C., $T_G^E$ is ≦270° C., $T_B^E$ is ≦275° C.; or $T_W^{ein,E}$ (and if appropriate $T_W^E$) ≧290° C., $T_G^E$ ≦270° C., $T_B^E$ ≦270° C.; or $T_H^{in,E}$ (and if appropriate $T_W^E$) is ≧290° C., $T_G^E$ is ≦270° C., $T_B^E$ is ≦265° C.; or $T_H^{in,E}$ (and if appropriate $T_W^E$) is $\geq 290°$ C., $T_G^E$ is $\leq 270°$ C., $T_B^E$ is $\leq 260°$ C.

Moreover, the aforementioned temperature triples (or else if appropriate temperature quadruples) are suitable for an advantageous inventive startup, except that $T_H^{in,E}$ (and if appropriate $T_H^E$) is $\geq 291°$ C., or $\geq 292°$ C., or $\geq 293°$ C., or $\geq 294°$ C., or $\geq 295°$ C., or $\geq 297°$ C., or $\geq 299°$ C., or $\geq 300°$ C., or $\geq 305°$ C., or $\leq 310°$ C., or $\geq 315°$ C., or $\geq 320°$ C., or $\geq 330°$ C., or $\geq 340°$ C.

Appropriately from an application point of view, $T_B^E$ in the process according to the invention will be above the dew point (preferably at least 5° C. above) of the reaction gas entry mixture.

The process according to the invention is quite generally primarily a process for restarting a heterogeneously catalyzed partial gas phase oxidation of acrolein to acrylic acid or of methacrolein to methacrylic acid. Such a restart process is not performed on a freshly prepared fixed catalyst bed freshly filled into the tube bundle reactor. Instead, it is performed on a fixed catalyst bed over which a heterogeneously catalyzed partial gas phase oxidation of acrolein to acrylic acid or of methacrolein to methacrylic acid has already been performed beforehand.

In this document, a reaction gas entry mixture shall be understood to mean a gas mixture which comprises at least 3% by volume, preferably at least 4% by volume and more preferably at least 5% by volume (based on the total volume of the reaction gas entry mixture) of acrolein or methacrolein. Typically, the reaction gas entry mixture will comprise from 3 to 15% by volume, in many cases from 4 to 10% by volume, in many cases from 5 or 6 to 8% by volume, of acrolein or methacrolein. When gas mixtures which comprise less than 3% by volume of acrolein or methacrolein are conducted through the fixed catalyst bed (such gases may also be used as "cooling gases" which will be mentioned later in this document), this shall likewise be understood as an interruption of the partial oxidation like when no gas mixture is conducted through the fixed catalyst bed of the tube bundle reactor. With increasing content of acrolein or methacrolein in the reaction gas entry mixture (and with increasing loading of the fixed catalyst bed with reaction gas entry mixture or with acrolein or methacrolein in the reaction gas entry mixture), the process according to the invention gains significance. Correspondingly, the higher the content of acrolein or methacrolein in the reaction gas entry mixture, the lower $T_B^E$ and, if appropriate, also $T_G^E$ should be selected. Even in the case of increased oxygen contents in the reaction entry mixture, such lower values are advisable.

The molar ratio of $O_2$:acrolein in the reaction gas entry mixture will normally be $\geq 0.5$, frequently $\geq 1$. Typically, this ratio will be at values of $\leq 3$. Frequently, the molar ratio of $O_2$:acrolein in the reaction gas entry mixture is from 0.5 or 1 to 2, or from 0.6 or 1 to 1.5.

The molar ratio of $O_2$:methacrolein in the reaction gas entry mixture will frequently be from 1 or 1.5 to 3, or advantageously from 1.5 to 2.5. It may also be from 0.5 to 3.

Moreover, the reaction gas entry mixture will generally comprise at least one inert diluent gas which, minus $O_2$ and acrolein or methacrolein, in its entirety essentially forms the remainder of the reaction gas entry mixture. In this document, this shall be understood to mean those gases which, when the reaction gas entry mixture is conducted through the fixed catalyst bed disposed in the tube bundle reactor in the course of an inventive startup, remain unchanged to an extent of at least 95 mol %, preferably to an extent of at least 98 mol %, most preferably to an extent of at least 99 mol % or to an extent of at least 99.5 mol %.

Typical inert diluent gases are molecular nitrogen, steam, noble gases, $CO_2$, and saturated hydrocarbons such as methane, ethane, propane, butane and pentane, and also mixtures of portions or of the entirety of the aforementioned diluent gases.

Typically, the inert diluent gas in the reaction gas entry mixture may consist of molecular nitrogen to an extent of $\geq 20\%$ by volume, or to an extent of $\geq 30\%$ by volume, or to an extent of $\geq 40\%$ by volume, or to an extent of $\geq 50\%$ by volume, or to an extent of $\geq 60\%$ by volume, or to an extent of $\geq 70\%$ by volume, or to an extent of $\geq 80\%$ by volume, or to an extent of $\geq 90\%$ by volume, or to an extent of $\geq 95\%$ by volume.

Especially when the gas phase partial oxidation of acrolein (or of methacrolein) is the second reaction stage of a two-stage heterogeneously catalyzed partial gas phase oxidation of propylene to acrylic acid, the inert diluent gas of the reaction gas entry mixture will frequently consist of $H_2O$ to an extent of from 5 to 25% by weight, or to 20% by weight (is formed in the first reaction stage and added if appropriate) and of $N_2$ to an extent of from 70 to 90% by volume.

Frequently, in processes according to the invention, the reaction gas entry mixture will have an acrolein (methacrolein):oxygen:steam:other inert gas volume ratio (l (STP)) of 1:(1 to 3):(0 to 20):(3 to 30), preferably of 1:(1 to 3):(0.5 to 10):(7 to 10), or, in the case of acrolein, of 1:(0.9 to 1.3):(2.5 to 3.5):(10 to 12) and, in the case of methacrolein, of 1:(1.5 to 2.5):(3 to 6):(10 to 15).

The entrance pressure of the reaction gas entry mixture on entry into the orifice E (absolute pressure) may be either below standard pressure (for example up to 0.5 bar) or above standard pressure. Typically, the aforementioned working pressure will be at values of from 1 to 5 bar, frequently from 1 to 3 bar. The aforementioned working pressure normally will not exceed 100 bar.

The loading of the fixed catalyst bed with acrolein or methacrolein may, in the inventive startup, be $\geq 10$ l (STP)/(l·h), or $\geq 20$ l (STP)/(l·h), or $\geq 30$ l (STP)/(l·h), or $\geq 40$ l (STP)/(l·h), or $\geq 50$ l (STP)/(l·h), or $\geq 60$ l (STP)/(l·h), or $\geq 70$ l (STP)/(l·h), or $\geq 80$ l (STP)/(l·h), or $\geq 90$ l (STP)/(l·h), or $\geq 110$ l (STP)/(l·h), or $\geq 130$ l (STP)/(l·h), or $\geq 180$ l (STP)/(l·h), or $\geq 240$ l (STP)/(l·h), or $\leq 300$ l (STP)/(l·h) (but normally $\leq 600$ l (STP)/(l·h)). The aforementioned loading may also be increased in stages in the course of the inventive startup, as described, for example, in WO 2005/016861 for the startup of a freshly charged fixed catalyst bed and in WO 2005/047226 for the startup of a freshly regenerated fixed catalyst bed. The loading of the fixed catalyst bed with reaction gas entry mixture may, in an inventive startup, simultaneously to the aforementioned framework, typically be from 500 to 10 000 l (STP)/(l·h), usually from 1000 to 5000 l (STP)/(l·h), frequently from 1500 to 4000 l (STP)/(l·h).

Otherwise, the inventive startup is, advantageously from an application point of view, effected such that at no point along the catalyst tubes is the temperature of the reaction gas mixture in the reaction tube more than 80° C. higher than the temperature of the heat exchange medium at the same reaction tube length in the reaction tube surrounding space. Advantageously, the aforementioned temperature difference at every point along the reaction tubes is $\leq 70°$ C., frequently from 20 to 70° C.; this temperature difference is preferably small.

Moreover, the process according to the invention is suitable, inter alia, in the case of tube bundle reactors which satisfy the requirements according to DE 20 2006 014 116 U1.

The reactor jacket normally has a cylindrical geometry with a circular cross section of the tube plates. Typical cross-sectional areas of the tube plates (and also of the reactor plate E) are from 3 m² to 80 m², often from 10 m² to 50 m². The tube plate thickness (and also of the reactor plate E) is generally from 5 to 40 cm, frequently from 8 to 30 cm or from 10 to 20 cm. The larger the tube plate cross section, the greater the tube plate thickness normally is.

The reaction tubes are (just like the other elements of the tube bundle reactor), as already mentioned at the outset of this document, generally manufactured from steel. The inventive procedure is advantageous especially when the reactor plate surface E is manufactured from stainless steel (from austenitic steel) or from black steel (ferritic steel). The preferred material (also for the other elements of the tube bundle reactor) is ferritic steel. The wall thickness of the reaction tubes is typically from 1 to 3 mm. Their internal diameter is generally (uniformly) from 10 to 50 mm or from 20 to 30 mm, frequently from 21 to 26 mm. The number of catalyst tubes (reaction tubes) accommodated in the tube bundle reactor is generally at least 1000, or 3000, or 5000, preferably at least 10 000. Frequently, the number of reaction tubes accommodated in the tube bundle reactor is from 15 000 to 30 000 or to 40 000 or to 50 000. Tube bundle reactors having a number of reaction tubes above 50 000 are usually exceptional. Within the reactor jacket, the reaction tubes are normally arranged in homogeneous distribution, the distribution appropriately being selected such that the separation of the central internal axes of mutually closest catalyst tubes (reaction tubes) (the so-called catalyst tube pitch) is from 25 to 55 mm, frequently from 35 to 45 mm (cf., for example, EP-A 468 290).

Very particularly advantageously in accordance with the invention, the tube bundle reactor is manufactured from type 1.0425 ferritic steel (to DIN EN 10020). For the reactor plates, reaction tubes and reactor hoods, steel of DIN materials number 1.0481 or 1.0315 is frequently also used, and, for the reactor jacket, in many cases steel of DIN materials number 1.0345.

The inside of the reactor hood E facing the reactor plate surface E is, however, advantageously from an application point of view, plated with austenitic steel (preferably of DIN type 1.4541 or type 1.4571 (to DIN EN 10020)). Typical plating thicknesses are about 3 mm.

Especially in the case of tube bundle reactors with a relatively large cross section of their tube plates, it is appropriate from an application point of view to leave a tubeless region in the center of the tube bundle reactor, and instead to support the upper tube plate in this region. The length of the reaction tubes extends normally to a few meters (a typical catalyst tube length is in the range from 1 to 8 m, frequently from 2 to 6 m, in many cases from 2 to 4 m).

Within the reaction tubes, a differentiation is normally made between working tubes and thermal tubes. While the working tubes are those reaction tubes in which the partial oxidation to be performed in the actual sense is performed, thermal tubes primarily serve the purpose of monitoring and of controlling the reaction temperature along the reaction tubes in a representative manner for all working tubes. For this purpose, the thermal tubes normally comprise, in addition to the fixed catalyst bed, a thermowell which is conducted in the center along the thermal tube and is charged merely with a temperature sensor. In general, the number of thermal tubes in a tube bundle reactor is very much smaller than the number of working tubes. Normally, the number of thermal tubes is $\leq 20$ (cf. EP-A 873 783 and EP-A 1 270 065).

The statement that the reaction tubes are sealed into the passage orifices in the upper and lower tube plates expresses that there is no means of passage for the heat exchange medium between the reaction tube outer wall and the bore wall (or the wall of the passage orifice or else shells of the passage orifice). Such a seal can be effected, for example, as described in DE 20 2006 014 116 U1.

In a corresponding manner, the circumference of the upper and lower tube plates is also incorporated into the reactor jacket of the tube bundle reactor such that there is no means of passage for the heat exchange medium between them. In the upper tube plate, however, there is generally a connection to the heat exchange medium pump which permits degassing of the reaction tube surrounding space and ensures that the liquid heat exchange medium wets the upper tube plate (cf., for example, EP-A 987 057). Otherwise, a one-zone tube bundle reactor is preferably configured as described in DE-A 44 31 949.

When the process according to the invention is performed in a multizone tube bundle reactor, it is, advantageously from an application point of view, a two-zone tube bundle reactor.

When that reaction zone which the reaction gas mixture flows through first is referred to as reaction zone A and that reaction zone which the reaction gas mixture flows through thereafter as reaction zone B, the inventive startup is advantageously performed such that the difference between the highest reaction temperature occurring in reaction zone A in the course of startup (referred to hereinafter as $T^{maxA}$) and the highest reaction temperature occurring in the course of startup in reaction zone B (referred to hereinafter as $T^{maxB}$), i.e. $T^{maxA} - T^{maxB}$, is $\geq 0°$ C. Advantageously, the aforementioned temperature difference is $\geq 3°$ C. and $\leq 60°$ C., especially advantageously $\geq 5°$ C. and $\leq 40°$ C. This is generally the case when the difference between the entrance temperature of the heat exchange medium into reaction zone A, i.e. $T_H^{A,in}$, and the entrance temperature of the heat exchange medium into reaction zone B, i.e. $T_H^{B,in}$, (i.e. $T_H^{A,in} - T_H^{B,in}$) is $\geq -20°$ C. and $\leq 0°$ C.

Otherwise, the procedure for adjusting $T^{maxA}$ and $T^{maxB}$ may be as described in the documents DE-A 103 13 208, EP-A 1 106 598, DE-A 103 13 213, DE-A 103 13 214, DE-A 103 13 211 and US 2006/0161019 A1, and the prior art cited in these documents. In particular, the two-zone tube bundle reactors described in these documents are suitable for a process according to the invention. In general, in both reaction zones, reaction gas and heat exchange medium, viewed over the particular reaction zone, are conducted either in cocurrent or in countercurrent. It is, however, possible without any problem to employ cocurrent operation in one of the two reaction zones and countercurrent operation in the other of the two reaction zones.

In order to adjust the temperature $T_B^E$ of the reactor plate surface E, it is possible in a simple manner, immediately before the reaction gas entry mixture is fed through the orifice E to the tube bundle reactor, for example, to conduct an essentially inert gas or gas mixture at such a flow rate and with a sufficiently low temperature through the at least one orifice E that the reactor plate surface E cools to the desired surface temperature $T_B^E$. Useful such cooling gases C include, for example, steam, molecular nitrogen, carbon dioxide, molecular oxygen, noble gases, air, and mixtures of any type of all or of portions of the aforementioned gases. In principle, the cooling gas mixture used should comprise <3% by volume, better <2% by volume, or <1% by volume, and especially advantageously no acrolein and no methacrolein.

For example, useful cooling gases C include mixtures of inert gas and molecular oxygen. These may comprise at least 1 or 2% by volume, preferably at least 3% by volume and more preferably at least 4% by volume of oxygen. In general, the oxygen content of the cooling gas mixture will, however, be ≦21% by volume. For example, a useful such cooling gas mixture is lean air. This is air depleted in oxygen. An advantageous gas in accordance with the invention is lean air which consists of from 3 to 10% by volume, preferably from 4 to 6% by volume, of molecular oxygen and, as the remainder, of molecular nitrogen. Frequently, it is advantageous when the cooling gas mixture, as well as molecular oxygen and inert gas, additionally comprises steam. Appropriately from an application point of view, the cooling gas mixture comprises at least 0.1% by volume, frequently at least 0.5% by volume and often at least 1% by volume of steam. Normally, the steam content of the cooling gas mixture is ≦75% by volume, frequently ≦50% by volume, in many cases ≦25% by volume. Gas mixtures suitable as cooling gas may thus, for example, consist of from 3 to 20% by volume of molecular oxygen, from 1 to 75% by volume of steam and, as the remainder, of inert gas such as $N_2$ and $CO_2$ (for example 97% by volume of air and 3% by volume of steam).

It will be appreciated that useful cooling gases C are also those which simultaneously exert a regenerating effect on the fixed catalyst bed. In other words, useful cooling gases are, for example, all gases and gas mixtures recommended as regenerating gases in DE-A 10350822, US 2006/0161019, WO 2005/042459 and in EP-A 614872.

In principle, it is advantageous when the molar specific heat of the cooling gas C is as high as possible.

Of course, it is also possible to use cycle gas or a mixture thereof (for example with air) comprising one or more of the other cooling gases C already mentioned as a cooling gas. Cycle gas refers to the residual gas which remains when the target product has been removed more or less selectively (for example by absorption into a suitable solvent) from the product gas mixture of a heterogeneously catalyzed partial gas phase oxidation.

In general, it consists predominantly of the inert diluent gases used for the partial oxidation and of steam typically formed as a by-product in the partial oxidation, and carbon oxides and steam formed by undesired full oxidation. If appropriate, steam stemming from an aqueous workup of the product gas mixture (from an aqueous absorbent for the target product) may also be present in the cycle gas. In some cases, it still comprises small amounts of oxygen unconsumed in the partial oxidation (residual oxygen) and/or of unconverted organic starting compounds (cf. WO 2004/007405).

A cycle gas of a two-stage heterogeneously catalyzed partial oxidation of propylene to acrylic acid which is suitable as a cooling gas before the inventive startup may, for example, typically have the following contents:

| | |
|---|---|
| 3 to 5% by volume of | molecular oxygen, |
| 1 to 5% by volume of | steam, |
| 0 to 3% by volume of | carbon monoxide, |
| 0 to 8% by volume of | carbon dioxide, |
| 0 to 2% by volume of | propane, |
| 0 to 0.5% by volume of | propylene, |
| 0 to 0.1% by volume of | acrolein, and |
| 85 to 95% by volume of | molecular nitrogen. |

An example of a cycle gas composition from the aforementioned framework is as follows:

| component | % by volume |
|---|---|
| oxygen | 3.3, |
| water | 1.5, |
| carbon monoxide | 0.8, |
| carbon dioxide | 1.6, |
| propane | 0.3, |
| propene | 0.3, |
| acrolein | 0.05, and |
| nitrogen | 92.15. |

It will be appreciated that, within the aforementioned cycle gas composition framework, the propane content may also be up to 50% by volume and the nitrogen content may be correspondingly lower.

In the case of a heterogeneously catalyzed partial gas phase oxidation for preparing methacrylic acid, a typical cycle gas composition may, for example, have the following contents:

| | |
|---|---|
| 5 to 12% by volume of | molecular oxygen, |
| 10 to 25% by volume of | steam, |
| 0 to 4% by volume of | carbon monoxide, |
| 0 to 6% by volume of | carbon dioxide, |
| 0 to 0.5% by volume of | isobutene, |
| 0 to 0.2% by volume of | methacrolein, and |
| 50 to 90% by volume of | molecular nitrogen. |

The temperature with which the cooling gas C is fed into the orifice E to the tube bundle reactor must, in accordance with the invention, necessarily be ≦285° C. Frequently, the aforementioned cooling gas temperature will be ≦280° C., or ≦270° C., or ≦260° C., or ≦250° C., or ≦240° C., or ≦230° C, or ≦220° C, or ≦210° C., or ≦200° C., or ≦190° C., or ≦180° C., or ≦170° C., or ≦160° C., or ≦150° C., or ≦140° C., or ≦130° C., or ≦120° C., or ≦110° C., or ≦100° C. In principle, the temperature of the cooling gas may, though, also be ≦75° C., or ≦50° C., or ≦25° C. and ≦0° C.

What is essential is, however, that the temperature of the cooling gas is above the dew point of the cooling gas. Appropriately in accordance with the invention, the temperature of the cooling gas is at least 5° C. above the dew point of the cooling gas. The working pressure of the cooling gas when it passes through the orifice E may be 1 bar, <1 bar or >1 bar. Frequently, this working pressure of the cooling gas will be from ≧0.5 bar to 5 bar, in many cases from >1 to 3 bar, often from ≧1.3 to ≦2 bar. Advantageously, the cooling gas C is compressed in the same manner and subjected to a mechanical separating operation for the purpose of removing solid particles and, if appropriate, condensate present therein as described by documents WO 2005/016852 and WO 2005/100290 for the reaction gas entry mixture.

The volume flow rate of the cooling gas may correspond to that of the reaction gas entry mixture.

However, it may also be greater than the volume flow rate of the reaction gas entry mixture or less than the volume flow rate of the reaction gas entry mixture. Advantageously in accordance with the invention, it is from 20 to 140%, advantageously from 40 to 120% and especially advantageously from 60 to 100% of that volume flow rate which the reaction gas entry mixture of the heterogeneously catalyzed partial gas phase oxidation had before it was interrupted.

Based on the cross-sectional area of the reactor plate E (including the passage orifices), the flow rate of the cooling gas C is, appropriately from an application point of view, from 500 to 3000 m³ (STP)/(h·m²), frequently from 750 to 1500 m³ (STP)/(h·m²).

The temperature of the reactor plate surface E can be monitored with the aid of at least one thermocouple countersunk into the reactor plate surface E.

Advantageously in accordance with the invention, the cooling gas supply is terminated when the temperature $T_B^E$ contemplated for the reactor plate surface E has been attained.

The higher $T_H^{in,E}$ and the lower the cooling gas flow, of course, the longer this duration of cooling gas supply must be.

Since the cooling gas C also flows through the reaction tubes, the cooling of the reactor plate surface E can, in an undesired manner, also be accompanied by cooling of the heat exchange medium conducted through the corresponding reaction tube surrounding space (section) (in these cases, configurations of inventive startup can result in which $T_H^{in,E}$ and $T_H^E$ are different from one another; in general, $T_H^E$ in these cases will be below $T_H^{in,E}$). Appropriately in accordance with the invention, attempts are made to avoid this. If appropriate, an electrical heater generally integrated in a tube bundle reactor unit will be used to counteract any excessive cooling of the heat exchange medium which sets in.

When the heterogeneously catalyzed partial gas phase oxidation of acrolein to acrylic acid or of methacrolein to methacrylic acid is the second oxidation stage in a two-stage process or heterogeneously catalyzed partial gas phase oxidation of propylene (or propane) via acrolein to acrylic acid or of, for example, isobutene (or tert-butanol or the methyl ether of tert-butanol or isobutane) via methacrolein to methacrylic acid, this second oxidation stage will frequently be performed as an independent one-zone or multizone tube bundle reactor in a tandem reactor arrangement (series connection of two tube bundle reactors). Appropriately in accordance with the invention, in this case, an intermediate cooler (or aftercooler), which may also be integrated into the first tube bundle reactor, is disposed between the tube bundle reactor for the first oxidation stage and the tube bundle reactor for the second oxidation stage. In this case, the cooling gas is normally fed to the reactor plate surface E of the second tube bundle reactor via the first tube bundle reactor (i.e. through the reaction tubes thereof, which generally has the same design as the second tube bundle reactor. Since the temperature of the at least one heat exchange medium in the first tube bundle reactor is normally above that of the at least one heat exchange medium in the second tube bundle reactor, the cooling temperature of the cooling gas for the reactor plate surface E is then set in a simple manner in the above-described intermediate cooler.

Appropriately from an application point of view, the procedure will be such that, in the first tube bundle reactor too, with regard to the analogous reactor plate surface E*, cooling to a temperature below that analogous $T_H^{in,E*}$ (and if appropriate $T_H^{E*}$) of the heat exchange medium which wets this reactor plate is brought about. However, the situation in the first oxidation stage is significantly less critical than in the second oxidation stage.

Advantageously, in the startup of the first oxidation state, too, the temperature of the reactor plate surface E* will be at least 5° C., preferably at least 10° C., especially preferably at least 20 or at least 30° C., very especially preferably at least 40 or at least 50° C. below that temperature that the heat exchange medium wetting this reactor plate has as $T_H^{in,E*}$ (and if appropriate $T_H^{E*}$).

It will be appreciated that, in the startup of the first oxidation stage, the temperature of the reactor plate surface E* may also be at least 60 or 70° C., or at least 80 or 90° C., in some cases even at least 100° C. or at least 150° C. and more below that temperature which the heat exchange medium which wets this reactor plate E* has as $T_H^{in,E*}$ (and if appropriate $T_H^{E*}$). In an entirely corresponding manner, the temperature of the reaction gas entry mixture for the heterogeneously catalyzed partial gas phase oxidation of propylene to acrolein or of isobutene to methacrolein will also be at least 5° C., or at least 10° C., or at least 20° C., or at least 30° C., or at least 40° C., or at least 50° C., or at least 60° C., or at least 70° C., or at least 80° C., or at least 90° C., or at least 100° C., below the temperature $T_H^{in,E*}$ (and if appropriate $T_H^{E*}$) of that heat exchange medium which wets the reactor plate E*. The temperature $T_H^{in,E*}$ (and if appropriate $T_H^{E*}$) of that heat exchange medium which wets the reactor plate E* may generally be from 300 to 380° C., frequently from 310 to 360° C. and in many cases from 320 to 340° C.

In the first oxidation stage too, the fixed catalyst bed in the reaction tubes will generally have, in flow direction, first an inert bed which serves to heat the reaction gas entry mixture.

Since, in a two-stage partial oxidation in a tandem tube bundle reactor arrangement as described above, the product gas mixture of the first oxidation stage, after cooling in the aftercooler as required, forms the reaction gas entry mixture for the second oxidation stage either directly as such (in which case the oxygen requirement for the second oxidation stage is already part of the reaction gas entry mixture for the first oxidation stage as so-called primary oxygen) and/or after addition of air (secondary air) in a mixer, and an interruption of the partial oxidation in the second oxidation stage is necessarily accompanied by an interruption of the first oxidation stage, the startup of the second oxidation stage in these cases is normally also always associated with a startup of the first oxidation stage.

Appropriately from an application point of view, this is undertaken in accordance with the remarks in the documents WO 2004/007405, WO 2005/016861, WO 2004/085362, WO 2004/085369, WO 2004/085363, WO 2004/085367, WO 2004/085368, WO 2005/047224 and WO 2005/042459 such that the requirements in this application are satisfied for an inventive startup especially of the second oxidation stage.

Advantageously, in an inventive startup, the procedure will be to undertake the required cooling of the reactor plate surface E initially with cycle gas or with cycle gas and steam in a mixture (this type of adjustment of the temperature $T_B^E$ required in accordance with the invention can already set in immediately with commencement of the interruption of the partial oxidation; it will be appreciated that regeneration gas can also first be conducted through the tube bundle reactor system according, for example, to DE-A 10350822 or DE-A 10350812 from interruption of the partial oxidation). The cycle gas flow rate and its temperature will be such that the desired temperature $T_B^E$ is achieved without significantly impairing the temperature control circulation of the at least one liquid heat exchange medium. Before the startup at the latest, the cycle gas flow rate or the cycle gas/steam mixture flow rate will be adjusted to the magnitude corresponding to its gas volume flow rate fraction in the reaction gas entry mixture stream in the inventive startup.

Subsequently, the air stream required for the inventive startup (generally, the oxygen source used is air; in principle, it is, though, possible to use any mixtures of oxygen and inert gas or else pure oxygen as the oxygen source) and finally the reactant stream will be switched on. It will be appreciated that $T_B^E$ can in principle also be adjusted by using a mixture of cycle gas and air to which the reactant stream is finally switched. When the inventive startup is effected as a startup of the second oxidation stage in a two-stage partial oxidation of, for example, propylene (via acrolein) to acrylic acid or of, example, isobutene (via methacrolein) to methacrylic acid in a tandem tube bundle reactor arrangement, the aforementioned gas streams, as described above, are fed to the tube bundle reactor of the first oxidation stage and reach, supplemented if appropriate by secondary air, via its reaction tubes and intermediate cooler, the reactor plate surface E.

The process according to the invention is suitable especially for restarting after an interruption of the relevant partial oxidation of at least 5 minutes, or of at least 10 minutes, or of at least 15 minutes, or of at least 20 minutes, or of at least 30 minutes, or of at least 1 hour, or of at least 2 hours, or of at least 3 hours, or of at least 4 hours, or of at least 6 hours, or of at least 7 hours, or of at least 8 hours, or of at least 9 hours, or of at least 10 hours or of at least 11 hours, or of at least 12 hours or more.

After the inventive adjustment of the temperature of the reactor plate surface E and if appropriate E*, in the event of interruptions of the relevant partial oxidation of up to 12 hours, the inventive startup of the partial oxidation will, appropriately from an application point of view, be undertaken essentially with that composition of the reaction gas entry mixture and loading of the particular fixed catalyst bed with this mixture with which the partial oxidation was operated immediately before its interruption, even when, within the interruption period, according to documents DE-A 103 50 812, DE-A 103 50 822 and WO 2005/047226, a regenerating molecular oxygen-comprising gas stream is conducted through the particular fixed catalyst bed.

When the interruption period is above 12 h and the procedure during this period is as in documents DE-A 103 50 822, DE-A 10350812 and WO 2005/047226, the composition of the reaction gas entry mixture and the progress in the loading of the fixed catalyst bed with this mixture will, appropriately from an application point of view, be practised as described in DE-A 103 37 788.

The risk of an undesired thermally initiated exothermic homogeneous combustion of acrolein or methacrolein present in the reaction gas entry mixture which spreads from the reactor plate surface E in the opposite direction to the flow direction of the reaction gas entry mixture can, in addition to the use of the inventive startup, be reduced by applying, to the reactor plate E, a bed of inert material whose thermal conductivity is very much lower (for example ceramic material) than that of the material from which the reactor plate E is manufactured. The inert bed preferably has a high heat capacity.

Useful materials for such an inert bed are in principle all of those materials which will be recommended hereinafter as materials for support bodies for preparing coated catalysts. An inert material preferred from an application point of view for such an inert bed is, for example, C 220 steatite from CeramTec. Useful geometric shaped bodies for the aforementioned inert bed include, for example, spheres, cylinders and/or rings whose longest dimension (longest direct line connecting two points on their surface) may, for example, be from 2 to 40 mm, preferably from 5 to 12 mm, or else from 50 to 200 mm. Appropriately from an application point of view, the aforementioned inert bed will, however, not take up more than 40% by volume of the internal volume of the reactor hood which spans it. A corresponding inert bed can be applied on the corresponding reactor plate E* of an upstream first oxidation stage. The curvature of the reactor hoods may, for example, have torispherical shape according to DIN 28013 or semiellipsoidal shape according to DIN 28011. In the simplest case, the reactor hood may also be reduced to an open cylindrical transition which leads, for example, to an aftercooler or leads away from an aftercooler. In principle, the transition from the reactor jacket to the reactor hood (which may be fluid in the exceptional case) is configured in an essentially gas-tight manner. In addition to the measures already described, in an inventive startup, the reactor plate E can also be thermally insulated against the heat exchange medium which wets it with the aid of a material having only a low thermal conductivity. Useful such materials include, for example, liquid heat exchange medium itself which essentially does not flow. This can be implemented, for example, by mounting a deflecting plate on the side of the tube plate facing the heat exchange medium just before the tube plate (the reactor plate E), beyond which the liquid heat exchange medium in the direction of the reactor plate E is essentially at rest.

Useful catalysts and shaped inert bodies for charging the reaction tubes of an upstream first oxidation stage and also a second oxidation stage to be started up in accordance with the invention include all of those which are recommended in the prior art (for example that cited in this document) for the partial oxidations.

These are especially those which are recommended in documents DE-A 103 50 822, WO 98/12167, DE-A 43 29 907, WO 2005/030393, DE 10 2004 025 445, EP-A 700 893, EP-A 700 714, EP-A 758 562, EP-A 1 388 533 and DE-A 103 51 269. The charging of the reaction tubes themselves can likewise be performed as recommended in these documents. In general, the charging is effected such that the volume-specific activity within the reaction tubes increases in flow direction of the reaction tube.

Useful inert shaped diluent bodies and/or support bodies (or shaped support bodies) for coated catalysts (onto which the active composition is applied; in contrast, unsupported catalysts consist essentially only of active composition) include porous or nonporous aluminum oxides, silicon oxide, thorium dioxide, zirconium oxide, silicon carbide, steatite (for example of type C 220 from CeramTec) or silicates such as magnesium silicate or aluminum silicate. Just like that of the shaped catalyst bodies, their longest dimension may be from 1 to 20 mm, often from 2 to 15 mm and in many cases from 3 or 4 to 10 or to 8 or to 6 mm.

In the case that the acrolein or methacrolein required for the process according to the invention is generated in an upstream heterogeneously catalyzed partial oxidation of propylene or, for example, isobutene, suitable catalysts are those whose active composition is a multielement oxide of the general formula I $$Mo_{12}Bi_aFe_bX_c^1X_d^2X_e^3X_f^4O_n \qquad (I)$$

where
$X^1$=nickel and/or cobalt,
$X^2$=thallium, an alkali metal and/or an alkaline earth metal,
$X^3$=zinc, phosphorus, arsenic, boron, antimony, tin, cerium, lead, vanadium, chromium and/or tungsten,
$X^4$=silicon, aluminum, titanium and/or zirconium,
$a$=0.2 to 5
$b$=0.01 to 5,
$c$=0 to 10,
$d$=0 to 2,
$e$=0 to 8,
$f$=0 to 10, and
$n$=a number which is determined by the valency and frequency of the elements in I other than oxygen.

Descriptions of the preparation of corresponding unsupported catalysts (for example rings) and coated catalysts (for example rings or spheres) can be found, for example, in WO 02/30569, in WO 2005/030393, in Research Disclosure RD 2005-497012, in DE-A 10 2007 005 602 and in DE-A 102007004961. In the case of ring geometry, the external diameter may be, for example, from 2 to 10 mm, or from 2 to 8 mm, or from 4 to 8 mm, or from 2 to 4 mm (the same applies in the case of sphere geometries). The length of these ring geometries may likewise be from 2 to 10 mm, or from 2 to 8 mm, or from 4 to 8 mm. The wall thickness of such ring geometries is appropriately from 1 to 3 mm. Aforementioned geometries are relevant especially in the case of unsupported catalysts. A particularly preferred ring geometry (especially in the case of unsupported catalysts) is, for example, the geometry of external diameter E 5 mm×length L 3 mm×internal diameter I 2 mm.

Other favorable multimetal oxide (I) unsupported catalyst ring geometries E×I×I are the geometries 5 mm×2 mm×2 mm, or 5 mm×3 mm×3 mm, or 5.5 mm×3 mm×3.5 mm, or 6 mm×3 mm×4 mm, or 6.5 mm×3 mm×4.5 mm, or 7 mm×3 mm×5 mm, or 7 mm×7 mm×3 mm, or 7 mm×7 mm×4 mm.

All of these multimetal oxide (I) unsupported catalyst ring geometries (or multimetal oxide (I) catalysts in general) are suitable both for the catalytic partial oxidation of propylene to acrolein in the gas phase and for the catalytic partial oxidation of iso-butene or tert-butanol or the methyl ether of tert-butanol to methacrolein in the gas phase.

Regarding the active compositions of the stoichiometry of the general formula I, the stoichiometric coeffecient b is preferably from 2 to 4, the stoichiometric coefficient c preferably from 3 to 10, the stoichiometric coefficient d preferably from 0.02 to 2, the stoichiometric coefficient e preferably from 0 to 5 and the stoichiometric coefficient f advantageously from 0.5 or 1 to 10. More preferably, the aforementioned stoichiometric coefficients are simultaneously within the preferred range mentioned.

Moreover, $X^1$ is preferably cobalt, $X^2$ is preferably K, Cs and/or Sr, more preferably K, $X^3$ is preferably tungsten, zinc and/or phosphorus, and $X^4$ is preferably Si. Especially preferably, the variables $X^1$ to $X^4$ simultaneously have the aforementioned definitions.

Annular (spherical) shaped catalyst bodies are, appropriately from an application point of view, diluted with annular (spherical) shaped inert bodies in order to bring about an activity structuring of the catalyst charge in the catalyst tube.

For a heterogeneously catalyzed partial gas phase oxidation to prepare acrolein or methacrolein, the catalyst charge in the reaction tube with the above-described annular shaped bodies is preferably either configured homogeneously with only one type of unsupported catalyst rings over the entire length of the reaction tube or structured as follows.

At the reaction tube inlet (in flow direction of the reaction gas mixture), for a length of from 10 to 60%, preferably from 10 to 50%, more preferably from 20 to 40% and most preferably from 25 to 35% (i.e., for example, for a length of from 0.70 to 1.50 m, preferably from 0.90 to 1.20 m), in each case of the total length of the catalytically active catalyst charge in the reaction tube, is placed a homogenized mixture of only one type of the aforementioned annular unsupported catalysts and only one type of annular shaped inert bodies (both shaped body types preferably have the same ring geometry), where the proportion by weight of the shaped diluent bodies (the bulk densities of shaped catalyst bodies and shaped diluent bodies generally differ only slightly) is normally from 5 to 40% by weight, or from 10 to 40% by weight, or from 20 to 40% by weight, or from 25 to 35% by weight. Downstream of this first charge section is then advantageously disposed, up to the end of the length of the catalyst charge (i.e., for example, for a length of from 1.00 to 3.00 m or from 1.00 to 2.70 m, preferably from 1.40 to 3.00 m or from 2.00 to 3.00 m), either a bed of the only one type of annular unsupported catalysts diluted only to a lower degree (than in the first section) with the only one type of annular shaped inert bodies, or, most preferably, a sole (undiluted) bed of the same only one type of annular unsupported catalyst. Of course, it is also possible to select a homogeneous dilution over the entire reaction tube length. The catalyst bed will be configured in a corresponding manner when the geometries are spherical.

Otherwise, the heterogeneously catalyzed partial gas phase oxidation of propylene to acrolein or of isobutene to methacrolein can be performed in a tube bundle reactor having one or more temperature zones as described in the prior art (cf., for example, WO 2005/03093, DE-A 10 2007 005 602 and DE-A 10 2004 025 445, and the prior art cited in these documents and in the present application).

Suitable active compositions for geometric shaped catalyst bodies for the heterogeneously catalyzed partial gas phase oxidation of methacrolein to methacrylic acid include multielement oxides of the general formula II

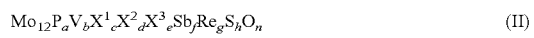   (II)

where
$X^1$=potassium, rubidium and/or cesium,
$X^2$=copper and/or silver,
$X^3$=cerium, boron, zirconium, manganese and/or bismuth,
a=0.5 to 3,
b=0.01 to 3,
c=0.2 to 3,
d=0.01 to 2,
e=0 to 2,
f=0.01 to 2,
g=0 to 1,
h=0 or 0.001 to 0.5, and
n=an integer which is determined by the valency and frequency of the elements in II other than oxygen.

Preference is given to aforementioned shaped catalyst bodies likewise annular unsupported catalysts, as obtainable, for example, by the procedure described in EP-A 467 144. Useful ring geometries include especially the individual geometries recommended in EP-A 467 144 and also those recommend with regard to the multielement oxides I in the present application. A preferred ring geometry is that where E×L×I=7 mm×7 mm×3 mm (cf. also DE-A 10 2007 005 602).

A structured dilution with annular shaped inert bodies can, for example, be effected as described for the case of the heterogeneously catalyzed partial oxidation of propylene to acrolein. Otherwise, the partial oxidation process conditions described in EP-A 467 144 and DE-A 10 2007 005 602 can be employed.

For the heterogeneously catalyzed partial gas phase oxidation of acrolein to acrylic acid, useful multielement oxide active compositions for shaped catalyst bodies to be used in the process according to the invention are advantageously those of the general formula III

   (III)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6
b=0.2 to 4,
c=0 to 18, preferably 0.5 to 18,
d=0 to 40,
e=0 to 2, f=0 to 4,
g=0 to 40, and
n=a number which is determined by the valency and frequency of the elements in IV other than oxygen.

Advantageously, these shaped catalyst bodies are annular or spherical coated catalysts, as obtainable, for example, according to DE-A 10 2004 025 445, DE-A 10 350 822, DE-A 10 2007 010 422, US 2006/0205978 and EP-A 714 700, and the prior art cited in these documents.

Useful ring geometries or sphere geometries are especially the individual geometries recommended in the aforementioned documents. A preferred ring geometry is that where E×L×I=7 mm×3 mm×4 mm for the parent annular shaped support bodies.

The active composition coating thickness may be from 10 to 1000 μm, preferably from 50 to 500 μm and more preferably from 150 to 250 μm. Favorable coating thicknesses are those of the exemplary embodiments of EP-A 714 700.

For a heterogeneously catalyzed partial gas phase oxidation of acrolein to acrylic acid, the catalyst charge in the reaction tube is preferably either structured uniformly with only one type of coated catalyst rings over the entire length of the reaction tube, or structured as follows.

At the reaction tube inlet (in flow direction of the reaction gas mixture), for a length of from 10 to 60%, preferably from 10 to 50%, more preferably from 20 to 40% and most preferably from 25 to 35% (i.e., for example, for a length of from 0.70 to 1.50 m, preferably from 0.90 to 1.20 m), in each case of the total length of the catalytically active catalyst charge in the reaction tube, is placed a homogenized mixture of only one type of the abovementioned annular coated catalysts and only one type of annular shaped inert bodies (both shaped body types preferably have the same ring geometry), where the proportion by weight of the shaped diluent bodies (the bulk densities of shaped catalyst bodies and of shaped diluent bodies generally differ only slightly) is normally from 5 to 40% by weight, or from 10 to 40% by weight, or from 20 to 40% by weight, or from 25 to 35% by weight. Downstream of this first charge section is then advantageously disposed, up to the end of the length of the catalyst charge (i.e., for example, for a length of from 2.00 to 3.00 m, preferably from 2.50 to 3.00 m), either a bed of the only one type of annular unsupported catalysts diluted only to a lesser extent (than in the first section) with the only one type of annular shaped inert bodies, and/or, most preferably a sole (undiluted) bed of the same only one type of annular coated catalyst. The fixed catalyst bed will be configured in a corresponding manner when the coated catalyst geometry is spherical.

Otherwise, the heterogeneously catalyzed partial gas phase oxidation of acrolein to acrylic acid can be performed in a tube bundle reactor having one or more temperature zones, as described in the prior art (cf., for example, DE-A 10 2004 025 445, DE-A 103 50 822, DE-A 10 2007 010 422, EP-A 700 893, US 2006/0205978 and EP-A 714 700, and the prior art cited in these documents).

According to the above, the present invention thus relates not least to processes for preparing acrylic acid or methacrylic acid which comprise a process according to the invention.

The process according to the invention is particularly relevant when the reaction gas entry mixture and the heat exchange medium which wets the reactor plate surface E are conducted in countercurrent viewed over the tube bundle reactor. However, it is also of significance in the case of such a cocurrent flow thereof.

Generally, the fixed catalyst bed both for the inventive partial oxidation and for a partial oxidation stage preceding it will be configured such that, when they are started up, as described in EP-A 990636 and in EP-A 1106598, both the hotspot formation and their thermal sensitivity are at a minimum. Otherwise, the reactant conversions and the selectivities of product formation when partial oxidations are started up (based on single pass through the fixed catalyst bed) correspond essentially to those in the regular operation of the partial oxidation.

The numbers in FIGS. 1 to 4 have the following meaning:

FIG. 1: shows a schematic of a one-zone tube bundle reactor

FIG. 2: shows a schematic of a two-zone tube bundle reactor

FIGS. 3, 4: show schematics of usable deflecting plate combinations

| | | |
|---|---|---|
| 1 = | | reaction gas entry mixture |
| 2 = | | product gas mixture |
| 3 = | | orifice E |
| 4 = | | reactor plate surface E |
| 5 = | | lower reactor plate |
| 6 = | | reactor hood E |
| 7 = | | lower reactor hood |
| 8 = | | motor for the pump of the heat exchange medium |
| 9 = | | reaction tube |
| 10 = | | removal of the heat exchange medium with $T_H^{out}$ |
| 11 = | | supply of the heat exchange medium with $T_H^{in}$ |
| 12 = | | supply of a portion of heat exchange medium for cooling |
| 13 = | | return of the cooled portion of heat exchange medium |
| 14 = | | reactor jacket |
| 15 = | | reaction tube surrounding space |
| 16 17 18 | = | deflecting plates for the heat exchange medium |
| 19 = | | reactor plate E |
| A = | | reaction zone A |
| B = | | reaction zone B |
| 20 = | | separating tube plate |

In particular, the present invention relates to a process for restarting-up a heterogeneously catalyzed partial gas phase oxidation, whose operation has had to be interrupted beforehand, of acrolein to acrylic acid or of methacrolein to methacrylic acid in a fixed catalyst bed which is disposed in a tube bundle reactor in the reaction tubes of a vertical bundle of reaction tubes surrounded by a reactor jacket, both ends of the individual reaction tubes being open and the upper end of each reaction tube ending sealed into a passage orifice of an upper tube plate sealed at the top into the reactor jacket and the lower end ending sealed into a passage orifice of a lower tube plate sealed at the bottom into the reactor jacket, the exterior of the reaction tubes, the upper and the lower tube plate and the reactor jacket together delimiting the reaction tube surrounding space, and each of the two tube plates being spanned by a reactor hood having at least one orifice, in which, in order both to begin the restart and to maintain operation, a reaction gas entry mixture comprising ≧3% by volume of acrolein or methacrolein and also molecular oxygen is fed to the reaction tubes of the tube bundle reactor via the at least one orifice, referred to hereinafter as E, in one of the two reactor hoods, and the product gas mixture which results through partial gas phase oxidation of acrolein or methacrolein to acrylic acid or methacrylic acid in the course of passage through the fixed catalyst bed disposed in the reaction tubes and comprises acrylic acid or methacrylic acid is removed via the at least one orifice of the other reactor hood, while, on the jacket side of the tube bundle reactor, at least one liquid heat exchange medium is conducted around the reaction tubes such that each of the two surfaces of the two tube plates facing one another are wetted by a liquid heat exchange medium and the at least one liquid heat exchange medium is conducted into the reaction tube surrounding space with the temperature $T_H^{in}$ and is conducted out of the reaction tube surrounding space again with the temperature $T_H^{out}$, wherein A) at the time $t_1$ at which the heterogeneously catalyzed partial gas phase oxidation has been interrupted, the temperature $T_H^{in}$, referred to hereinafter as $T_H^{in, U}$, of the at least one liquid heat exchange medium which wets the reactor plate E is at least 290° C., and B) at the time $t_2$ at which, in order to begin the restart of the heterogeneously catalyzed partial gas phase oxidation, the reaction gas entry mixture comprising ≧3% by volume of acrolein or methacrolein enters the reactor hood through the at least one orifice E the temperature $T_H^{in}$, referred to hereinafter as $T_H^{in, I}$ of the at least one Iquid heat exchange medium which wets the reactor plate E is at least 290° C., the reaction gas entry mixture which enters the at least one orifice E has a temperature $T_G^E$ of ≦285° C., and the temperature $T_B^E$ of the reactor plate surface E has a value of ≦285° C. as a result of the fact that, between the time $t_1$ and the time $t_2$, a cooling gas C whose temperature $T_C^E$ was ≦285° C. had been conducted at least temporarily through the at least one orifice E.

It will be appreciated that, in the present process for restart, the following conditions may also be simultaneously fulfilled:

$T_H^{in, U}$≧292° C., $TH^{in, I}$≧292° C., $T_G^E$≦285° C., $T_B^E$≦285° C., $T_C^E$≦285° C.; or $T_H^{in, U}$≧294° C., $T_H^{in, I}$≧294° C., $T_G^E$≦285° C., $T_B^E$≦285° C., $T_C^E$≦285° C.; or $T_H^{in, U}$≧296° C., $T_H^{in, I}$≧296° C., $T_G^E$≦285° C., $T_B^E$≦285° C., $T_C^E$≦285° C.; or $T_H^{in, U}$≧298° C., $T_H^{in, I}$≧298° C., $T_G^E$≦285° C., $T_B^E$≦285° C., $T_D^E$≦285° C.; or $T_H^{in, U}$≧300° C., $T_H^{in, I}$≧300° C., $T_G^E$≦285° C., $T_B^E$≦285° C., $T_C^E$≦285° C.

In general, $T_H^{in, U}$ and $T_H^{in, I}$ in the aforementioned cases will be ≦400° C., frequently ≦375° C. and in some cases ≦350° C. Irrespective of the other temperatures in the aforementioned framework, $T_G^E$ may also be ≦280° C., or ≦270° C., or ≦260° C., or ≦250° C., or ≦240° C. Likewise, $T_B^E$ within the aforementioned framework, irrespective of the other temperatures, may be ≦280° C., or ≦275° C., or ≦270° C., or ≦265° C., or ≦255° C., or ≦250° C., or ≦245° C., or ≦240° C. Equally, $T_C^E$, irrespective of the other temperatures in the above framework, may also be ≦280° C., or ≦275° C., or ≦270° C., or ≦265° C., or ≦260° C., or ≦255° C., or ≦250° C., or ≦245° C., or ≦240° C.

Comparative examples and example with reference to a two-stage heterogeneously catalyzed partial gas phase oxidation of propylene to acrylic acid in two one-zone tube bundle reactors connected in series A) Description of the General Process Conditions
   I. The First Reaction Stage

| | |
|---|---|
| Heat exchange medium used: | Salt melt consisting of 60% by weight of potassium nitrate and 40% by weight of sodium nitrite. |
| Material of the reaction tubes: | Ferritic steel of DIN materials number 1.0481. |
| Dimensions of the reaction tubes: | length 3200 mm; internal diameter 25 mm; external diameter 30 mm (wall thickness: 2.5 mm). |
| Number of reaction tubes in the tube bundle: | 25500. |
| Reactor: | Cylindrical vessel (ferritic steel of DIN materials number 1.0345) of an external diameter of 6800 mm; jacket wall thickness = 1.8 cm in the middle part, thickened to 2.5 cm at the top and bottom; annular vertical tube bundle with a free central space. |

Diameter of the central free space: 1000 mm. Distance of the outermost reaction tubes from the vessel wall: 150 mm. Homogeneous reaction tube distribution in the tube bundle (6 equidistant neighboring tubes per reaction tube).

Reaction tube pitch: 38 mm.

The ends of the reaction tubes were secured with sealing into orifices of tube plates of plate thickness 125 mm and their orifices opened into a reactor hood which spans the upper reactor plate and is connected to the vessel at the upper end, and at the lower end into the cylindrical transition to the aftercooler.

The upper tube plate is the reactor plate E*. The reactor hood which spans it had an orifice E* (in the form of a gas inlet stub) with a diameter of 1020 mm.

The tube plates and the other elements of the tube bundle reactor were manufactured from ferritic steel of DIN materials number 1.0481. A thermocouple was admitted or introduced in each case into the reactor plate surface E* (at the outermost reaction tube circle) and into the upper reactor hood (the reactor hood E*). The upper reactor hood (total wall thickness=20 mm) was plated on the inside with stainless steel of the 1.4571 type (to DIN EN 10020) (plating thickness: 3 mm).

Feeding of the heat exchange medium to the tube bundle: The tube bundle was divided into 4 equidistant (in each case 730 mm) longitudinal sections (zones) by three deflecting disks (thickness in each case 10 mm) mounted successively between the tube plates in the longitudinal direction thereof.

The lowermost and the uppermost deflecting disk had ring geometry with an internal ring diameter of 1000 mm, and the external ring diameter extended up to and was sealed to the vessel wall. The reaction tubes were secured on the deflecting disks without sealing. Instead, a gap having a gap width of <0.5 mm was left such that the transverse flow rate of the salt melt within one zone was substantially constant.

The middle deflecting disk was circular and extended up to the outermost reaction tubes of the tube bundle.

The circulation of the salt melt was accomplished by two salt pumps, each of which supplied one half of the tube bundle length.

The pumps injected the salt melt into an annular channel mounted around the reactor jacket, which distributed the salt melt over the vessel circumference. The salt melt passed through windows present in the reactor jacket in the lowermost longitudinal section to the tube bundle. The salt melt then flowed, dictated by the deflecting plates, in the sequence from the outside inward,
from the inside outward,
from the outside inward,
from the inside outward, in an essentially meandering manner viewed over the vessel, from the bottom upward. The salt melt collected through windows mounted around the vessel circumference in the uppermost longitudinal section (the salt melt left the reaction tube surrounding space with the temperature $T_H^{1,out}$) in an upper annular channel mounted around the reactor jacket, and was, after cooling to the original entrance temperature $T_H^{1,in}$, injected back into the lower annular channel by the pumps.

The reaction gas entry mixture 1 was a mixture of air, chemical-grade propylene and cycle gas.

Reactor charge: Salt melt and reaction gas mixture were conducted in countercurrent viewed over the reactor. The salt melt entered at the bottom, the reaction gas mixture via the orifice E* at the top.

The entrance temperature of the salt melt was $T_H^{1,in}$. The exit temperature of the salt melt was $T_H^{1,out}$. $T_H^{1,out} - T_H^{1,in}$ was >0 and ≦2° C.

The pump output was 6200 m³ of salt melt/h.

The reaction gas entry mixture 1 was fed to the reactor with a temperature of $T_G^{E*,1}$ when it passed through the orifice E*.

Propylene loading of the
fixed catalyst bed 1: It was $L^1 l$ (STP)/(l·h).
Reaction tube charge with fixed
catalyst bed 1
(from the top downward): Zone A: 50 cm Preliminary bed of steatite rings of geometry 7 mm×3 mm×4 mm (external diameter×length×internal diameter)

Zone B: 100 cm

Catalyst charge with a homogeneous mixture of 30% by weight of steatite rings of geometry 5 mm×3 mm×2 mm (external diameter×length×internal diameter) and 70% by weight of an annular unsupported catalyst which, like unsupported catalyst EUC 3 from WO 2005/030393, has been prepared using TIMREX T 44 from Timcal AG (Bodio, Switzerland) as auxiliary graphite and, without taking account of graphite still present, had the stoichiometry $Mo_{12}Bi_1W_2Co_{5.5}Fe_{2.94}Si_{1.59}K_{0.08}O_x$ with the ring geometry E×L×I=5 mm×3 mm×2 mm.

Zone C: 170 cm

Catalyst charge only with the annular (5 mm×3 mm×2 mm=external diameter×length×internal diameter) unsupported catalyst used for zone B.

Thermal tubes (they numbered 10 and were distributed uniformly in the central region of the tube bundle) were configured and charged as follows in order to monitor the temperature in the reaction tubes in a representative manner.

Each of the 10 thermal tubes had a central thermowell with 40 temperature measurement points (i.e. each thermal tube comprised 40 thermocouples which were integrated at different length into a thermowell and thus formed a multithermocouple with which the temperature could be determined simultaneously at different heights within the thermal tube).

20 of the 40 temperature measurement points in each case were present in the region of the first meter of the active section of the fixed catalyst bed (in flow direction of the reaction gas mixture).

The internal diameter of one thermal tube was 29 mm. The wall thickness and the tube material were configured as for the working tubes.

The external diameter of the thermowell was 10 mm.

The thermal tubes were filled as follows:

A thermal tube was filled with the annular unsupported catalyst from zone B. In addition, catalyst spall of longest dimension from 0.5 to 5 mm obtained from the annular unsupported catalyst was filled into the thermal tube.

The catalyst spall was filled in homogeneous distribution over the entire active section of the fixed catalyst bed of the particular thermal tube such that the pressure drop of the reaction gas mixture in the course of passage through the thermal tube corresponded to that in the course of passage of the reaction gas mixture through a working tube (based on the active section of the fixed catalyst bed (i.e. excluding the inert sections), from 5 to 30% by weight of catalyst spall were required for this purpose in the thermal tube). At the same time the particular total fill height of active and inert sections in the working and thermal tubes was equalized and the ratio of total amount of active composition present in the tube to heat transfer area of the tube in working and thermal tubes was adjusted to essentially the same value.

II. The Intermediate Cooling

The acrolein-comprising product gas mixture 1 leaving the first reaction stage with a temperature corresponding to the salt melt entrance temperature $T_H^{1,in}$ was, for the purpose of intermediate cooling, conducted through a one-zone tube bundle heat exchanger made of ferritic steel and cooled with a salt melt composed of 60% by weight of potassium nitrate and 40% by weight of sodium nitrite, which was flanged directly onto the lower tube plate of the tube bundle reactor of the first reaction stage. The distance of the lower tube plate of the tube bundle reactor from the upper tube plate of the cooler was 10 cm. The salt melt and the product gas mixture were conducted in countercurrent viewed over the heat exchanger. The salt bath itself flowed in the same way as in the first-stage one-zone tube bundle fixed bed reactor in a meandering manner around the cooling tubes through which the product gas mixture 1 was passed. The length of the cooling tubes was 1.65 m, their internal diameter was 2.6 cm and their wall thickness was 2.5 mm. The cooling tubes numbered 8000. The external diameter of the heat exchanger was 6.8 m; the wall thickness corresponded to that of the reactor.

They were distributed uniformly over the cross section with homogeneous tube pitch.

Spirals of stainless steel whose cross section corresponded virtually to that of the cooling tubes were introduced into the entrance of the cooling tubes (in flow direction). Their length was from 700 mm to 1000 mm (alternatively, the cooling tubes can be filled with large inert material rings). They serve to improve the heat transfer.

The acrolein-comprising product gas mixture 1 left the immediate cooler with a temperature $T_G^{Z,out}$. Subsequently, compressed air (secondary air) having a temperature of 140° C. was added to it in such an amount that the oxygen content in product gas mixture 2 was 3.0% by volume, which resulted in the composition of the reaction gas entry mixture 2 for the second reaction stage.

This was fed with its temperature $T_G^{E,2}$ into the orifice E of the upper reactor hood of the one-zone tube bundle tube fixed bed reactor of the second reaction stage.

III. The Second Reaction Stage

A one-zone tube bundle fixed bed reactor identical in design to that of the first stage except that it had an upper and a lower reactor hood was used. Its upper reactor plate is the reactor plate E with the reactor plate surface E facing the upper reactor hood E.

The composition of the reaction gas entry mixture 2 consisted of the product gas mixture of the first reaction stage and the secondary air.

Reactor charge: Salt melt and reaction gas mixture were conducted in countercurrent viewed over the reactor. The salt melt entered at the bottom, the reaction mixture at the top.

The entrance temperature of the salt melt was $T_H^{2,in}$. Its exit temperature was $T_H^{2,out}$.

$T_H^{2,out} - T_H^{2,in}$ was >0 and ≦2° C.

The pump output was 6200 m³ of salt melt/h.

The reaction gas entry mixture 2 was fed to the reactor with a temperature of $T_G^{E,2}$ when it passed through the orifice E.

The acrolein loading of the
fixed catalyst bed 2: It was $L^2$ I (STP)/(l·h).
The reaction tube charge with fixed catalyst bed 2
(from the top downward) was: Zone A:

20 cm preliminary bed of steatite rings of geometry 7 mm×3 mm×4 mm (external diameter×length×internal diameter).

Zone B:

100 cm catalyst charge of a homogeneous mixture of 30% by weight of steatite rings of geometry 7 mm×3 mm×4 mm (external diameter×length×internal diameter) and 70% by weight of the annular (approx. 7 mm×3 mm×4 mm) coated catalyst $C_A$ from DE 10 2004 025 445 with the active composition $Mo_{12}V_3W_{1.2}Cu_{2.4}O_x$ and an active composition content of 20% by weight.

Zone C:

200 cm of catalyst charge of the annular (approx. 7 mm×3 mm×4 mm) coated catalyst from zone B.

Thermal tubes (they numbered 10 and were distributed uniformly in the central region of the tube bundle) were configured and charged as follows in order to monitor the temperature in the reaction tubes in a representative manner.

Each of the 10 thermal tubes had a central thermowell with 40 temperature measurement points (i.e. each thermal tube comprised 40 thermocouples which were integrated at different length into a thermowell and thus formed a multithermocouple with which the temperature could be determined simultaneously at different heights within the thermal tube).

20 of the 40 temperature measurement points in each case were present in the region of the first meter of the active section of the fixed catalyst bed (in flow direction of the reaction gas mixture).

The internal diameter of one thermal tube was 29 mm. The wall thickness and the tube material were configured as for the working tubes.

The external diameter of the thermowell was 10 mm.

The thermal tubes were filled as follows:

A thermal tube was filled with the annular coated catalyst prepared. In addition, two geometries of spherical coated catalysts were filled into the thermal tube (same active composition as the annular coated catalyst; the diameter of the two types of steatite C220 (CeramTec) support spheres was 2-3 mm and 4-5 mm; the active composition content in both cases was 20% by weight; the preparation was effected as described for the annular coated catalyst, except that the binder was a corresponding amount of water).

The spherical coated catalysts were filled in homogeneous distribution over the entire active section of the fixed catalyst bed of the particular thermal tube such that the pressure drop of the reaction gas mixture when it passed through the thermal tube corresponded to that when the reaction gas mixture passed through a working tube (based on the active section of the fixed catalyst bed (i.e. excluding the inert sections), a total of from 5 to 40% by weight of the spherical coated catalysts were required for this purpose in the thermal tube). At the same time, the particular total fill height of active and inert sections in the working and thermal tubes was equalized and the ratio of total amount of active composition present in the tube to heat transfer area of the tube in working and thermal tubes was adjusted to the same value.

The product gas mixture 2 obtained in the second reaction stage was conducted out through the lower reactor hood of the tube bundle reactor and sent to its workup.

The conversion was monitored and controlled in the two reaction stages generally with reference to the residual propylene and acrolein contents in the product gas mixture 2.

B) Results (Operating Years Always Relates to an $L^1$ of 130 l (STP)/(l·h) and the composition of the Reaction Gas Entry Mixture Specified with Regard to this Load)

1. Startup of the one-zone partial oxidation after the fixed catalyst bed 1 in the first reaction stage has been replaced by a fresh fixed catalyst bed 1, while the fixed catalyst bed 2 in the second reaction stage has been replaced one operating year (including regeneration according to DE-A 10350822 and DE-A 10351269) beforehand by a fresh fixed catalyst bed 2 (comparative example; the lifetime of fixed catalyst bed 1 is generally longer than that of fixed catalyst bed 2, which is why the two fixed catalyst beds are generally exchanged at different times). However, the fixed catalyst bed 2 may, according to DE-A 10350822, also be freshly regenerated.

Table 1 below indicates the conditions for the startup over the operating time t [h]. $C^P$ is the conversion of propylene based on single pass of the reaction gas mixture through the two oxidation stages.

$C^{AC}$ is the conversion of acrolein in single pass of the reaction gas mixture through the second reaction stage.

In addition, table 1 shows the composition of the reaction gas entry mixture 1. In the table:

c(Pen)=its propylene content in % by volume;
c($O_2$)=its oxygen content in % by volume;
c($H_2O$)=its steam content in % by volume;
c(CO)=its carbon monoxide content in % by volume;
c($CO_2$)=its carbon dioxide content in % by volume,
c($N_2$)=its nitrogen content in % by volume.

The selectivity of acrolein formation in the first reaction stage was always in the range from 88 to 92 mol %. The selectivity of acrylic acid by-product formation in the first reaction stage was always in the range from 3 to 7 mol %. The selectivity of acrylic acid formation over the two reaction stages was always in the range from 88 to 92 mol %.

An acrolein content originating from the cycle gas content of the reaction gas entry mixture 1 (which was <0.1% by volume) was neglected.

The loadings $L^1$ and $L^2$ are understood to mean L±5 l (STP)/(l·h). When the regular (that desired for the steady state) operational loading L1 is at values of <190 l (STP)/(l·h), the operating values can be maintained at a steady state from the attainment of this target load. $C^P$ should, however, not be increased to 96.2 mol % before the 20th operating day. The reaction gas entry pressure was always from 1800 to 3400 mbar in the first reaction stage and always from 1500 to 2800 mbar in the second reaction stage.

TABLE 1

| t (h) | $L^1$ [l(STP)/(l·h)] | $L^2$ [l(STP)/(l·h)] | $T_H^{1,in}$ (°C.) | $T_G^{E*,1}$ (°C.) | $T_H^{2,in}$ (°C.) | $T_G^{E,2}$ (°C.) | $C^P$ (mol %) | $C^{Ac}$ (mol %) |
|---|---|---|---|---|---|---|---|---|
| 0 to 24 | 60 | 41 | 310 | 300 | 255 | 240 | 92 | 99.2 |
| >24 to 48 | 80 | 55 | 314 | 300 | 258 | 240 | 92 | 99.3 |
| >48 to 264 | 100 | 71 | 320 | 300 | 264 | 240 | 95 | 99.4 |
| >264 to 288 | 110 | 79 | 322 | 300 | 266 | 240 | 95 | 99.4 |
| >288 to 312 | 120 | 86 | 325 | 300 | 268 | 240 | 95 | 99.4 |
| >312 to 336 | 130 | 93 | 328 | 300 | 270 | 240 | 95 | 99.4 |
| >336 to 360 | 140 | 100 | 331 | 300 | 272 | 240 | 95 | 99.4 |
| >360 to 504 | 150 | 108 | 334 | 300 | 274 | 240 | 95 | 99.4 |
| >504 to 528 | 190 | 137 | 330 | 300 | 272 | 240 | 96.2 | 99.4 |

The data in the last line relate to two-zone operation in each of the two reaction stages.
$T_H^{1,in}$ and $T_H^{2,out}$ relate in each case to the first temperature zone in flow direction of the reaction gas.

| t (h) | c (Pen) | c ($O_2$) | c ($H_2O$) | c (CO) | c ($CO_2$) | c ($N_2$) |
|---|---|---|---|---|---|---|
| 0 to 24 | 5.2 | 9.3 | 1.4 | 0.5 | 1.4 | 82.2 |
| >24 to 48 | 5.2 | 9.3 | 1.4 | 0.5 | 1.1 | 82.5 |
| >48 to 264 | 6.0 | 10.4 | 1.4 | 0.4 | 0.9 | 80.9 |
| >264 to 288 | 6.0 | 10.4 | 1.4 | 0.4 | 0.9 | 80.9 |
| >288 to 312 | 6.0 | 10.4 | 1.4 | 0.4 | 0.9 | 80.9 |
| >312 to 336 | 6.0 | 10.4 | 1.4 | 0.4 | 0.9 | 80.9 |
| >336 to 360 | 6.0 | 10.4 | 1.4 | 0.4 | 0.9 | 80.9 |
| >360 to 504 | 6.3 | 10.8 | 1.3 | 0.4 | 0.8 | 86.7 |
| >504 to 528 | 6.3 | 10.8 | 1.3 | 0.4 | 0.8 | 86.7 |

The aforementioned startup conditions can also be employed when both fixed catalyst bed 1 and fixed catalyst bed 2 have been freshly charged. They can also be employed when fixed catalyst bed 1 has been freshly charged and, in fixed catalyst bed 2, according to DE-A 10232748 and WO 2004/009525, only a portion has been replaced by a fresh fixed catalyst bed charge.

2. The startup described in B) 1. can be performed in a corresponding manner with secondary air metering when both fixed catalyst bed 1 and fixed catalyst bed 2 are disposed in a two-zone tube bundle reactor, as described in WO 2004/085369, but with an intermediate cooler disposed between the two reaction stages. Under the prerequisite of a fixed catalyst bed and heating zone configuration as specified in the working example of the aforementioned document (except using the catalysts from B) 1. of the present application), the reaction gas mixture entry compositions and the loading changes over the operating time will be configured in a corresponding manner as described in B) 1. The same applies to $C^P$ and $C^{Ac}$. The entrance temperature of the salt melt into the first reaction zone of the first reaction stage in flow direction is selected such that $C^P$ over this first reaction zone is from 65 to 70 mol % (it is normally below the corresponding $T_H^{1,in}$ in one-zone operation). The entrance temperature of the salt melt into the first reaction zone of the second reaction stage in flow direction is selected such that $C^{Ac}$ over this first reaction zone is from 80 to 85 mol % (it is normally below the corresponding $T_H^{2,in}$ in one-zone operation).

3. Startup of the one-zone partial oxidation after fixed catalyst bed 2 has been replaced completely by a fresh catalyst bed or, as described in WO 2004/009525, partly replaced, while fixed catalyst bed 1 in the first reaction stage has been replaced one operating year beforehand by a fresh fixed catalyst bed 1 (comparative example; fixed catalyst bed 1 can, however, be freshly regenerated according to WO 2005/047224).

Table 2 below indicates the conditions for the startup over the operating time t [h]. Like in table 1, it also shows the composition of the reaction gas entry mixture 1.

The selectivity of acrolein formation in the first reaction stage is always in the range from 88 to 92 mol %. The selectivity of acrylic acid by-product formation in the first reaction stage was always in the range from 3 to 7 mol %.

The selectivity of acrylic acid formation over the two reaction stages was always in the range from 88 to 92 mol %.

An acrolein content originating from the cycle gas content of the reaction gas entry mixture 1 (which was <0.1% by volume) was neglected.

The loadings $L^1$ and $L^2$ are understood to mean L±5 l (STP)/(l·h). When the regular (that desired for the steady state) operational loading is at values of <190 l (STP)/(l·h), the operating values can be maintained in a steady state in the course of startup from attainment of this target load. The reaction gas entrance pressure was always from 1800 to 3400 mbar in the first reaction stage and always from 1500 to 2800 mbar in the second reaction stage.

TABLE 2

| t (h) | $L^1$ [l(STP)/(l·h)] | $L^2$ [l(STP)/(l·h)] | $T_H^{1,in}$ (°C.) | $T_G^{E*,1}$ (°C.) | $T_H^{2,in}$ (°C.) | $T_G^{E,2}$ (°C.) | $C^P$ (mol %) | $C^{Ac}$ (mol %) |
|---|---|---|---|---|---|---|---|---|
| 0 to 1 | 60 | 42 | 315 | 300 | 255 | 240 | 95 | 98.5 |
| >1 to 2 | 80 | 57 | 320 | 300 | 257 | 240 | 95 | 98.5 |
| >2 to 3 | 100 | 71 | 323 | 300 | 258 | 240 | 95 | 98.5 |
| >3 to 4 | 100 | 71 | 324 | 300 | 258 | 240 | 95.5 | 98.7 |
| >4 to 24 | 100 | 72 | 324 | 300 | 258 | 240 | 95.8 | 98.7 |
| >24 to 48 | 100 | 72 | 324 | 300 | 259 | 240 | 95.8 | 99.0 |
| >48 to 72 | 100 | 72 | 324 | 300 | 260 | 240 | 95.8 | 99.3 |
| >72 to 96 | 130 | 94 | 332 | 300 | 266 | 240 | 96.2 | 99.4 |

TABLE 2-continued

| | | | | | | | | |
|---|---|---|---|---|---|---|---|---|
| >96 to 108 | 140 | 101 | 334 | 300 | 267 | 240 | 96.2 | 99.4 |
| >108 to 120 | 150 | 108 | 336 | 300 | 269 | 240 | 96.2 | 99.4 |
| >120 to 132 | 160 | 116 | 324 | 300 | 265 | 240 | 96.2 | 99.4 |
| >132 to 144 | 170 | 123 | 326 | 300 | 267 | 240 | 96.2 | 99.4 |
| >144 to 156 | 180 | 130 | 330 | 300 | 269 | 240 | 96.2 | 99.4 |
| >156 to 168 | 190 | 137 | 334 | 300 | 270 | 240 | 96.2 | 99.4 |

The data in the last four lines relate to two-zone operation in each of the two reaction stages.
$T_H^{1,in}$ and $T_H^{2,in}$ relate in each case to the first temperature zone in flow direction of the reaction gas.

| t (h) | C (Pen) | C ($O_2$) | C ($H_2O$) | C (CO) | C ($CO_2$) | C ($N_2$) |
|---|---|---|---|---|---|---|
| 0 to 1 | 5.2 | 9.3 | 1.4 | 0.5 | 1.0 | 82.6 |
| >1 to 2 | 5.2 | 9.3 | 1.4 | 0.5 | 1.0 | 82.6 |
| >2 to 3 | 5.2 | 9.3 | 1.4 | 0.5 | 1.0 | 82.6 |
| >3 to 4 | 5.7 | 10.0 | 1.4 | 0.4 | 1.0 | 81.5 |
| >4 to 24 | 6.0 | 10.4 | 1.4 | 0.4 | 0.9 | 80.9 |
| >24 to 48 | 6.0 | 10.4 | 1.4 | 0.4 | 0.9 | 80.9 |
| >48 to 72 | 6.0 | 10.4 | 1.4 | 0.4 | 0.9 | 80.9 |
| >72 to 96 | 6.3 | 10.8 | 1.3 | 0.4 | 0.8 | 80.4 |
| >96 to 108 | 6.3 | 10.8 | 1.3 | 0.4 | 0.8 | 80.4 |
| >108 to 120 | 6.3 | 10.8 | 1.3 | 0.4 | 0.8 | 80.4 |
| >120 to 132 | 6.3 | 10.8 | 1.3 | 0.4 | 0.8 | 80.4 |
| >132 to 144 | 6.3 | 10.8 | 1.3 | 0.4 | 0.8 | 80.4 |
| >144 to 156 | 6.3 | 10.8 | 1.3 | 0.4 | 0.8 | 80.4 |
| >156 to 168 | 6.3 | 10.8 | 1.3 | 0.4 | 0.8 | 80.4 |

4. The startup described in B) 3. can be performed in a corresponding manner with secondary air metering when both fixed catalyst bed 1 and fixed catalyst bed 2 are disposed in a two-zone tube bundle reactor as described in WO 2004/085369, but with an intermediate cooler disposed between the two reaction stages. Under the prerequisite of a fixed catalyst bed as specified in the working example of the aforementioned document—and temperature zone configuration (except using the catalysts from B) 1. of the present application), the reaction gas mixture entry composition and the load changes will be configured over the operating time in a corresponding manner to that in B) 3. The same applies to $C^P$ and $C^{Ac}$. The entrance temperature into the first reaction zone of the first reaction stage in flow direction is selected such that $C^P$ over this first reaction zone is from 65 to 70 mol % (it is normally below the corresponding $T_H^{1,in}$ in one-zone operation). The entrance temperature of the salt melt into the first reaction zone of the second reaction stage in flow direction is selected such that $C^{Ac}$ over this first reaction zone is from 80 to 85 mol % (it is normally below the corresponding $T_H^{2,in}$ in one-zone operation).

5. Startup of the one-zone partial oxidation after catalyst bed 1 and catalyst bed 2 (including regeneration according to WO 2005/042459) have been operated together over one year and have just been freshly regenerated (comparative example). Before the last regeneration, $T_H^{1,in}$ was 332° C. and $T_H^{2,in}$ was 266° C.

Table 3 below indicates the conditions for the startup over the operating time t[h]. Like table 1, it also shows the composition of the reaction gas entry mixture 1.

The selectivity of acrolein formation in the first reaction stage was always in the range from 88 to 92 mol %. The selectivity of acrylic acid by-product formation in the first reaction stage was always in the range from 3 to 7 mol %.

The selectivity of acrylic acid formation over the two reaction stages was always in the range from 88 to 92 mol %.

An acrolein content originating from the cycle gas content of the reaction gas entry mixture 1 (which was <0.1% by volume) was neglected.

The loadings $L^1$ and $L^2$ are understood to mean L±5 l (STP)/(l·h). When the regular that desired for the steady state) operational loading is at values of >190 l (STP)/ (l·h), the operating values can be maintained in a steady state in the course of startup from attainment of this target load. The reaction gas entrance pressure was always from 1800 to 3400 mbar in the first reaction stage and always from 1500 to 2800 mbar in the second reaction stage.

The startup procedure described below can generally be employed when the two fixed catalyst beds have already been operated for a prolonged period (with intermediate regeneration) and have been freshly regenerated.

TABLE 3

| t (h) | $L^1$ [l(STP)/(l·h)] | $L^2$ [l(STP)/(l·h)] | $T_H^{1,in}$ (° C.) | $T_G^{E*,1}$ (° C.) | $T_H^{2,in}$ (° C.) | $T_G^{E,2}$ (° C.) | $C^P$ (mol %) | $C^{Ac}$ (mol %) |
|---|---|---|---|---|---|---|---|---|
| 0 to 1 | 60 | 42 | 310 | 300 | 256 | 240 | 95.0 | 99.2 |
| >1 to 2 | 80 | 57 | 315 | 300 | 259 | 240 | 95.0 | 99.2 |
| >2 to 4 | 100 | 71 | 321 | 300 | 261 | 240 | 95.6 | 99.3 |
| >4 to 11 | 100 | 72 | 323 | 300 | 261 | 240 | 95.8 | 99.4 |
| >11 to 12 | 110 | 80 | 326 | 300 | 264 | 240 | 96.2 | 99.4 |
| >12 to 13 | 120 | 87 | 328 | 300 | 265 | 240 | 96.2 | 99.4 |
| >13 to 25 | 130 | 94 | 330 | 300 | 267 | 240 | 96.2 | 99.4 |
| >25 to 37 | 140 | 101 | 333 | 300 | 269 | 240 | 96.2 | 99.4 |
| >37 to 49 | 150 | 108 | 335 | 300 | 272 | 240 | 96.2 | 99.4 |
| >49 to 61 | 160 | 116 | 323 | 300 | 266 | 240 | 96.2 | 99.4 |
| >61 to 73 | 170 | 123 | 324 | 300 | 267 | 240 | 96.2 | 99.4 |
| >73 to 85 | 180 | 130 | 327 | 300 | 269 | 240 | 96.2 | 99.4 |

TABLE 3-continued

| >85 to 90 | 190 | 137 | 330 | 300 | 271 | 240 | 96.2 | 99.4 |

The data in the last four lines relate to two-zone operation in each of the two reaction stages.
$T_H^{1,in}$ and $T_H^{2,in}$ relate in each case to the first temperature zone in flow direction of the reaction gas.

| t (h) | c (Pen) | c (O$_2$) | c (H$_2$O) | c (CO) | c (CO$_2$) | c (N$_2$) |
|---|---|---|---|---|---|---|
| 0 to 1 | 5.1 | 9.4 | 1.4 | 0.5 | 1.0 | 82.6 |
| >1 to 2 | 5.1 | 9.4 | 1.4 | 0.5 | 1.0 | 82.6 |
| >2 to 4 | 5.6 | 10.1 | 1.4 | 0.4 | 0.9 | 81.6 |
| >4 to 11 | 5.9 | 10.5 | 1.4 | 0.4 | 0.9 | 80.9 |
| >11 to 12 | 6.3 | 11.0 | 1.3 | 0.4 | 0.8 | 80.2 |
| >12 to 13 | 6.3 | 11.0 | 1.3 | 0.4 | 0.8 | 80.2 |
| >13 to 25 | 6.3 | 11.0 | 1.3 | 0.4 | 0.8 | 80.2 |
| >25 to 37 | 6.3 | 11.0 | 1.3 | 0.4 | 0.8 | 80.2 |
| >37 to 49 | 6.3 | 11.0 | 1.3 | 0.4 | 0.8 | 80.2 |
| >49 to 61 | 6.3 | 11.0 | 1.3 | 0.4 | 0.8 | 80.2 |
| >61 to 73 | 6.3 | 11.0 | 1.3 | 0.4 | 0.8 | 80.2 |
| >73 to 85 | 6.3 | 11.0 | 1.3 | 0.4 | 0.8 | 80.2 |
| >85 to 90 | 6.3 | 11.0 | 1.3 | 0.4 | 0.8 | 80.2 |

6. The startup described in B) 5. can be performed in a corresponding manner with secondary air metering when both fixed catalyst bed 1 and fixed catalyst bed 2 are disposed in a two-zone tube bundle reactor as described in WO 2004/085369, but with an intermediate cooler disposed between the two reaction stages. Under the prerequisite of a fixed catalyst bed as specified in the working example of the aforementioned document—and temperature zone configuration (except using the catalysts from B) 1. of the present application), the reaction gas mixture entry composition and the load changes will be configured over the operating time in a corresponding manner to that in B) 3. The same applies to $C^P$ and $C^{Ac}$. The entrance temperature into the first reaction zone of the first reaction stage in flow direction is selected such that $C^P$ over this first reaction zone is from 65 to 70 mol % (it is normally below the corresponding $T_H^{1,in}$ in one-zone operation). The entrance temperature of the salt melt into the first reaction zone of the second reaction stage in flow direction is selected such that $C^{Ac}$ over this first reaction zone is from 80 to 85 mol % (it is normally below the corresponding $T_H^{2,in}$ in one-zone operation).

7. (Example) Startup of the one-zone partial oxidation after fixed catalyst bed 1 and fixed catalyst bed 2 (including regeneration according to WO 2005/042459) have been operated together over four years and the partial oxidation has been interrupted for 2 h owing to an operational fault. During the interruption, a gas mixture composed of 4% by volume of O$_2$ and 96% by volume of N$_2$ was conducted through the tandem reactor arrangement with a loading of fixed catalyst bed 1 of 20 l (STP)/(l·h). Its entrance temperature into the orifice E* was 150° C. On entry into the orifice E, it had a temperature of 240° C. The salt melt temperatures $T_H^{1,in}$ of 348° C. and $T_H^{2,in}$ of 299° C. which exist before the interruption were maintained during the interruption.

Subsequently, the partial oxidation was to be continued again with $L^1$=130 l (STP)/(l·h) and c (Pen)=6.3 mol %, c (O$_2$)=11.0 mol %, and, as the remainder, essentially molecular nitrogen ($T_H^{1,in}$=348° C.; $T_H^{2,in}$=299° C.; $T_G^{E^*,1}$=300° C.; $T_G^{E,2}$=240° C.). The temperature $T_B^E$ of the reactor plate surface E was 298° C.

The production plant was shut down immediately, caused by a rapid rise in the temperature in the gas space of the reactor hood E.

Thereafter, for a period of 15 min, a stream of 35 000 Nm$^3$/h of nitrogen was conducted via the orifice E of the first reaction stage through the tandem reactor arrangement. On entry into the orifice E, this had a temperature of 220° C. The salt melt temperatures $T_H^{1,in}$ and $T_H^{2,in}$ were maintained unchanged. The temperature $T_B^E$ of the reactor plate surface E was reduced to 270° C. as a result. Subsequently, the production plant could be put into operation without any problem as described above. The acrolein concentration in the reaction gas entry mixture 2 in the second reaction stage was 4.6 mol %.

Finally, it should be stated that, in the case that the partial oxidation consists of two partial oxidation lines operated in parallel with, if appropriate, combined workup of the product gas mixture, one of the two production lines can be started up with the other line in production by using cycle gas obtained for the startup of the former with the latter in production.

Comparative examples and examples with reference to a one-stage heterogeneously catalyzed partial gas phase oxidation of methacrolein to methacrylic acid in a one-zone tube bundle reactor C) Description of the General Process Conditions in the Reaction Stage

| | |
|---|---|
| Heat exchange medium used: | Salt melt consisting of 60% by weight of potassium nitrate and 40% by weight of sodium nitrite. |
| Material of the reaction tubes: | ferritic steel of DIN materials number 1.0315. |
| Dimensions of the reaction tubes: | length 4500 mm; internal diameter 25 mm; external diameter 30 mm (wall thickness: 2.5 mm). |
| Number of reaction tubes in the tube bundle: | 25 000. |

Reactor (it was of the design and operating mode described in A) I. with the following essential deviations):

Cylindrical vessel (ferritic steel of DIN materials number 1.0425) of external diameter 6650 mm; jacket wall thickness=2.2 cm; annular vertical tube bundle with a free central space.

Diameter of the central free space: 1367 mm. Diameter of the outermost tube circle: 6472 mm. Homogeneous reaction tube distribution in the tube bundle (6 equidistant neighboring tubes per reaction tube).

Reaction tube pitch: 38 mm.

The ends of the reaction tubes were secured and sealed in orifices of tube plates of plate thickness 295 mm and their orifices opened into a reactor hood which spans the upper tube plate and is connected to the vessel at the upper end, and into a cylindrical transition to the aftercooler at the lower end. The aftercooler was of a type corresponding essentially to that from A) II. The cooling tubes numbered 7056. Their length was 1.4 m, their internal diameter 25 mm, their wall thickness 2 mm. The entrance temperature of the salt melt into the aftercooler was 222° C.

The upper tube plate is the reactor plate E. The reactor hood which spans it had an orifice E (in the form of a gas inlet stub) with an external diameter of 1016 mm and a wall thickness of 16 mm.

The tube plates were manufactured from ferritic steel of DIN materials number 1.0481 and the other elements of the tube bundle reactor from ferritic steel of DIN materials number 1.0315. A thermocouple was admitted or introduced in each case into the reactor plate surface E (at the outermost reaction tube circle) and into the upper reactor hood (reactor hood E). The upper reactor hood was, as in A) I., plated on the inside with stainless steel (DIN materials number 1.4541, layer thickness 3.5 mm).

The reaction gas entry mixture was a mixture of air, fresh methacrolein (Mac), steam and cycle gas. The air, the fresh methacrolein and the steam were taken up from the cycle gas system in the workup of the product gas mixture. The composition of the reaction gas entry mixture was, in normal operation, essentially:

c(Mac)=5.5 to 6.5% by volume,
c($O_2$)=9.5 to 11.0% by volume,
c($H_2O$)=19.0 to 22.0% by volume,
c(CO)=1.5 to 2.0% by volume,
c($CO_2$)=1.5 to 2.5% by volume,
c($N_2$)=essentially the remainder up to 100% by volume.

Reactor charge: Salt melt and reaction gas mixture were conducted in countercurrent viewed over the reactor. The salt melt entered at the bottom, the reaction gas mixture via the orifice E at the top.

The entrance temperature of the salt melt was $T_H^{in}$.

The exit temperature of the salt melt was $T_H^{out}$.

$T_H^{out} - T_H^{in}$ was >0 and ≤2° C.

The pump output was 4350 m³ of salt melt/h.

The reaction gas entry mixture was fed to the reactor with a temperature of $T_G^E$ when it passed through the orifice E.

Methacrolein loading of the
fixed catalyst bed: It was L I (STP)/(I·h).
Reaction tube charge with fixed
catalyst bed
from the top downward): Zone A: 50 cm
  Preliminary bed of steatite rings of geometry 7 mm×7 mm×4 mm (external diameter×length×internal diameter).
Zone B: 400 cm
  Catalyst charge of an annular unsupported catalyst which, like unsupported catalyst VUC 12 from DE 102005037678, had been prepared using TIMREX T 44 from Timcal AG (Bodio, Switzerland) as auxiliary graphite and, without taking account of graphite still present, had the stoichiometry $Mo_{12}P_{1.5}V_{0.6}Cs_{1/0}Cu_{0.5}Sb_1S_{0.04}O_x$ with the ring geometry E×L×I=7 mm×7 mm×3 mm.

Thermal tubes (they numbered 10 and were arranged uniformly in the central region of the tube bundle) were configured and charged in a manner analogous to that described in A) in order to monitor the temperature in the reaction tubes in a representative manner.

D) Results

1. Startup of the one-zone methacrolein partial oxidation after the fixed catalyst bed has been replaced by a fresh fixed catalyst bed (comparative example)

After the closure of the tube bundle reactor, first 30 t/h of air were conducted through the tube bundle reactor via the orifice E in the reactor hood E. This was sucked in from the environment by an overall compressor (before entry into the compressor, solid particles present therein and any condensate were removed as described in documents WO 2005/016852 and WO 2005/100290) and compressed to the entrance pressure of from 1.7 to 1.8 bar, in the course of which the air was heated and was at about 110° C. on entry into the orifice E. Later, a proportion of the air increasing over time was conducted through an indirect heat exchanger operated with steam (17 bar) before the compression and thus heated, which increased the temperature of the compressed air on entry into the orifice E gradually to 150° C. In order to increase this entrance temperature further, a portion of the hot air leaving the tube bundle reactor was recycled upstream of the compressor. The portions were such that the air temperature on entry into the compressor did not exceed 90° C. In this way, it was possible to increase the temperature of the compressed air on entry into the orifice E to about 180° C.

The amount of salt melt which remained in the tube bundle reactor during the exchange of the fixed catalyst bed and was converted to the solid state of matter therein was melted by the above-described passage of hot air through the tube bundle reactor. The overall compressor was then switched off (instead of 30 t/h of hot compressed air, now only 1000 m³ (STP)/h of a mixture (it was possible to withdraw it from a supply system with the required pressure) of 5% by volume of $O_2$ and 95% by volume of $N_2$ (lean air) with an entrance temperature of approx. 20° C. and the appropriate autogenous pressure of approx. 1.8 bar were conducted through the tube bundle reactor) and the salt pump was put into operation. On the route to the salt melt heat exchanger (which was not charged with cooling water at this time) was disposed an electrical heater with which the salt melt was heated to a $T_H^{in}$ of 278° C. within 30 h. At the same time, the total amount of salt melt from the corresponding reservoir was supplemented to its normal operating level. The lean air supply helped to bring the aftercooler of the reactor to operating temperature, which had now likewise been put into operation with hot salt melt.

The overall compressor was then switched on again and adjusted to its entry stream into the tube bundle reactor of 45 000 m³ (STP)/h. This value was always retained in the further process unless explicitly stated otherwise. The aqueous workup which was intended for the later removal of the methacrylic acid produced from the product gas mixture and had been charged with liquid water beforehand only at the beginning of the startup in order to wash the solid particles which stem from the catalyst filling (dust) out of the gas which carried them out of the tube bundle reactor with water for a short time had now likewise been put into operation.

The overall compressor conducted the total amount of gas already present in the system and maintained lean air supply through the aqueous workup in circulation (the leaving top pressure in the workup was 1.27 bar; recompression was effected to an entrance pressure of from 1.7 to 1.8 bar; the leaving temperature at the top of the workup was 66° C. (this is generally the case unless explicitly stated otherwise)), in the course of which the gas mixture took up steam (the outlet for the amounts of gas exceeding the control amount of 45 000 m³ (STP)/h was present as the offgas outlet in the workup) until, on entry into the orifice E, it had approximately a composition of 4% by volume of molecular oxygen, 21% by volume of steam and, as the remainder, essential nitrogen (the gas temperature on entry into the orifice E was about 110° C.).

The lean air supply was now switched off and, instead, 1000 kg/h of (previously filtered) air was supplied to the cycle gas system via an air compressor and the workup (the supply temperature into the workup was 60° C.). The oxygen concentration in the gas mixture supplied to the orifice E rose as a result. Once it reached 5% by volume (at 21% by volume of steam and, as the remainder, essentially nitrogen), 1000 kg/h of fresh methacrolein was supplied to the cycle gas system via the workup (feed temperature in the workup=37° C.; the gas temperature on entry of the gas mixture into the orifice E was about 110° C.).

The freshly supplied methacrolein had a purity of ≧95% by weight.

The significant impurities were from 3 to 4% by weight of water, approx. 1% by weight of methanol, and also small amounts of propionaldehyde, pentenal and formaldehyde. $T_H^{in}$ had now fallen to 276° C. caused by the gas cooling.

As soon as the oxygen content in the offgas had begun to decline and the $CO_2$ concentration in the essentially methacrolein-free offgas had begun to rise, the precompressed air stream supplied via the workup was increased until the oxygen concentration in the gas mixture entering the orifice E reached 5.6% by volume. While retaining the boundary conditions, the partial oxidation was operated thus over a further six minutes. At the end of this time period, the reaction gas entry mixture had the properties listed in table 4 below (part 1 and part 2), in each case in the first line of the table.

In the table:
c(Mac)=methacrolein content in % by volume,
c($O_2$)=oxygen content in % by volume,
c($H_2O$)=steam content in % by volume,
c(CO)=carbon monoxide content in % by volume,
c($N_2$)=nitrogen content in % by volume,
c($CO_2$)=carbon dioxide content in % by volume,
in each case of the reaction gas entry mixture.
In addition, in table 4:
$M^{Mac}$=stream of fresh methacrolein supplied to the cycle gas system via the workup in kg/h;

$C^{Mac}$=methacrolein conversion based on single pass of the reaction gas mixture through the tube bundle reactor in mol %;

$S^{Maa}$=selectivity of methacrylic acid formation based on methacrolein converted in single pass of the reaction gas mixture through the tube bundle reactor in mol %.

Later in the startup, the methacrolein concentration in the reaction gas entry mixture was increased gradually (by increasing the stream of fresh methacrolein). Air stream and $T_H^{in}$ were each, after the increase in $M^{Mac}$, readjusted correspondingly to the increase of c(Mac) with time, such that the results listed in table 4 resulted over the operating time t [h].

They were determined in each case at the end of the particular operating time interval at which a quasi-steady operating state corresponding to the accompanying new $M^{Mac}$ had been established in each case.

The values for L reported in table 4 are generally understood to mean L±2 I (STP)/(I·h).

Finally, it was possible to operate the partial oxidation further in an essentially steady state.

When, for example, owing to relatively low market demand, operation at lower loadings L is desired, it is of course possible to switch into the steady operating state as soon as it is reached.

TABLE 4

| t [h] | L [l (STP)/(l · h)] | $M^{Mac}$ [kg/h] | $T_H^{in}$ (° C.) | $T_G^E$ (° C.) | $C^{Mac}$ (mol %) | $D^{Maa}$ (mol %) |
|---|---|---|---|---|---|---|
| 0.1 | 7 | 1000 | 276 | 109 | 98 | — |
| >0.1 to 0.2 | 14 | 2000 | 277 | 110 | 95 | — |
| >0.2 to 0.5 | 18 | 2500 | 278 | 110 | 91 | — |
| >0.5 to 1.0 | 22 | 3000 | 277 | 111 | 89 | — |
| >1.0 to 19 | 31 | 3500 | 277 | 111 | 73 | 79.6 |
| >19 to 25 | 37 | 4000 | 278 | 111 | 70 | 79.4 |
| >25 to 95 | 46 | 4500 | 283 | 111 | 64 | 79.6 |
| >95 to 130 | 50 | 5000 | 285 | 111 | 65 | 80.4 |

| t (h) | c (Mac) | c ($O_2$) | c ($H_2O$) | c (CO) | c ($CO_2$) | c ($N_2$) |
|---|---|---|---|---|---|---|
| 0-0.1 | 0.8 | 5.6 | 21 | 3.7 | 6.0 | 63 |
| 0.1-0.2 | 1.6 | 6.9 | 21 | 3.0 | 4.5 | 63 |
| 0.2-0.5 | 2.0 | 8.0 | 21 | 2.8 | 3.6 | 63 |
| 0.5-1.0 | 2.5 | 8.3 | 21 | 2.8 | 3.5 | 62 |
| 1.0-19 | 3.8 | 9.0 | 21 | 2.1 | 2.5 | 62 |
| 19-25 | 4.6 | 9.2 | 21 | 2.1 | 2.5 | 61 |
| 25-95 | 5.4 | 9.6 | 21 | 1.9 | 2.3 | 60 |
| >95 to 130 | 5.9 | 9.9 | 21 | 1.8 | 2.2 | 60 |

2. (Comparison) Startup of the methacrolein partial oxidation after the fixed catalyst bed has been operated over a prolonged operating time (with intermediate regeneration according to JP-A 2003/30646) (as described in D) 1.) and the partial oxidation has been interrupted by an operational fault.

Before the interruption, the partial oxidation had been operated with L=55 I (STP)/(I·h). The supply of fresh methacrolein over the workup had been 4400 kg/h. The reaction gas entry mixture had essentially normal operation composition and $C^{Mac}$=53 mol % and $S^{Maa}$=83.4 mol % and $T_G^E$=111° C. and $T_H^{in}$=310° C.

During the interruption to operation, which lasted approx. 24 h, 4000 m³ (STP)/h of a regenerating gas mixture of composition 5.6% by volume of oxygen, 21 % by volume of steam and 73.4% by volume of nitrogen were conducted by means of the overall compressor through the orifice E (the entrance temperature of the gas mixture was 111° C.). $T_H^{in}$ was increased gradually to 314° C. over this period with the aid of an electrical heater (the salt melt vane with whose aid, as in each tube bundle reactor unit, the amount of salt melt which was removable for salt melt cooling was controllable was closed during this period).

Subsequently, the partial oxidation was to be continued essentially immediately in its normal operating state before the interruption (but with normal methacrolein load).

For this purpose, the gas stream conducted through the tube bundle reactor with the aid of the overall compressor was first, while maintaining an oxygen content of 5.6% by volume, increased to the normal operating control value of 45 000 m³ (STP)/h (cycle gas operation throughout the workup; gas entrance temperature=111° C.).

On attainment of a temperature of the reactor plate surface E of 305° C. ($T_H^{in}$=311° C.), the 5000 kg/h of fresh methacrolein were then supplied again via the workup, as a result of which a starting methacrolein concentration of 3.6% by volume and an oxygen content of 5.4% by volume were established in the reaction gas entry mixture. This led to an immediate shutdown of the production plant as a result of a rapid temperature rise in the reactor hood E.

3. (Example) Inventive startup of the methacrolein partial oxidation

After the immediate shutdown which occurred in D) 2., the tube bundle reactor was flushed with 1000 m³ (STP)/h of lean air (5% by volume of $O_2$, 95% by volume of $N_2$, entrance pressure=1.8 bar, entrance temperature=20° C.), and $T_H^{in}$ was simultaneously increased to 321° C. with the aid of the electrical heater. The lean air was then switched off, the air compressor was put back into operation and, with the aid of the overall compressor, in the cycle gas operation leading via the workup, a gas mixture of 5.6% by volume of oxygen, 21% by volume of steam and 73.4% by volume of nitrogen was conducted through the tube bundle reactor in a volume flow rate of 45 000 m³ (STP)/h and with an entrance temperature of 111° C. (orifice E; entrance pressure: 1.8 bar). In spite of opposing heating by means of the electrical heater, $T_H^{in}$ fell at the same time to 311° C. and the temperature of the reactor plate surface E fell to 257° C. While maintaining the $O_2$ concentration of 5.6% by volume, the feeding of 5000 kg/h of fresh methacrolein via the workup was now commenced. In parallel to the methacrolein content of the reaction gas entry mixture which was established at its steady-state value of 5.6% by volume starting from 3.6% by volume over time, its oxygen content was increased to 9.8% by volume. After 6 h, the steady operating state had been attained without incidence according to table 5.

TABLE 5

| L [l (STP)/(l·h)] | $M^{Mac}$ (kg/h) | $T_H^{in}$ (° C.) | $T_G^E$ (° C.) | $C^{Mac}$ (mol %) | $S^{Maa}$ (mol %) |
|---|---|---|---|---|---|
| 49 | 5000 | 311 | 110 | 66 | 82.0 |
| c (Mac) | c ($O_2$) | c ($H_2O$) | c (CO) | c ($CO_2$) | c ($N_2$) |
| 5.6 | 9.8 | 21 | 1.7 | 2.0 | 60 |

4. (Example) Inventive startup of the methacrolein partial oxidation

When the methacrylic acid production was interrupted again (operating conditions before the interruption (operation as described in D) 1.): Normal operating composition of the reaction gas entry mixture; $T_H^{in}$=312° C.; $C^{Mac}$=52 mol %; $S^{Maa}$=82.9 mol %, L=55 l STP)/(l·h)), 45 000 m³ (STP)/h of a gas mixture comprising 5.6% by volume of oxygen, 21% by volume of steam and 73.4% by volume of nitrogen (entrance temperature=111° C., entrance pressure=1.8 bar), with the aid of the overall compressor, via the workup in cycle gas mode, were first conducted through the tube bundle reactor for a period of 2 h. The gas flow-through was then switched to lean air for 48 h (1000 m³ (STP)/h; 5% by volume of $O_2$; 95% by volume of $N_2$; entrance temperature=20° C.; entrance pressure=1.8 bar). $T_H^{in}$ of 312° C. had initially been maintained. Then, in cycle gas mode, via the workup, with the aid of the overall compressor, 4000 m³ (STP)/h of a gas mixture comprising 5.6% by volume of oxygen, 21% by volume of steam and 73.4% by volume of nitrogen were conducted through the tube bundle reactor (entrance temperature=111° C., entrance pressure=1.8 bar). $T_H^{in}$ was simultaneously increased to 318° C. Thereafter, with the same oxygen content, the overall gas stream was increased to 45 000 m³ (STP)/h (entrance temperature=111° C., entrance pressure=1.8 bar).

At a temperature of the reactor plate surface E of 308° C. and $T_H^{in}$=315° C., the feeding of 1000 kg/h of fresh methacrolein via the workup was commenced (this corresponds to a starting methacrolein concentration in the reaction gas entry mixture fed to the tube bundle reactor of only 0.7 mol %; the oxygen content thereof was adjusted to the starting value of 5.6% by volume by adjusting the air supply). The entrance temperature $T_G^E$ was 111° C. and the entrance pressure was 1.8 bar. 5 minutes thereafter, the fresh methacrolein stream was increased to 2000 kg/h (this corresponds to a starting methacrolein concentration in the reaction gas entry mixture of 1.5% by volume; the oxygen content thereof was adjusted to the starting value of 7.0% by volume by adjusting the air supply; $T_G^E$=111° C.; entrance pressure=1.8 bar).

After maintaining the above operating conditions for 1 h, the temperature of the reactor plate surface E had fallen to 255° C. With inclusion of the electrical heater, it was possible to hold $T_H^{in}$ at 314° C.

The fresh methacrolein stream was now increased from 500 kg/h to 5000 kg/h with equidistant (time) steps within 1 h and the amount of air supplied via the workup was simultaneously readjusted so as to give rise to the $O_2$ volume fractions in the reaction gas entry mixture corresponding in each case to the particular corresponding fresh methacrolein stream in table 4. $T_H^{in}$ was left at 314° C. $T_G^E$ was a constant 111° C. and the entrance pressure was a constant 1.8 bar. The operating conditions were then maintained. 7 h later, the operating state indicated in table 6 had been attained.

TABLE 6

| L [l (STP)/(l·h)] | $M^{Mac}$ (kg/h) | $T_H^{in}$ (°C.) | $T_G^E$ (°C.) | $C^{Mac}$ (mol %) | $S^{Maa}$ (mol %) |
|---|---|---|---|---|---|
| 50 | 5000 | 314 | 109 | 65 | 81.4 |

| c (Mac) | c ($O_2$) | c ($H_2O$) | c (CO) | C ($CO_2$) | c ($N_2$) |
|---|---|---|---|---|---|
| 5.7 | 9.7 | 21 | 1.8 | 2.1 | 60 |

US Provisional patent application No. 60/907,954, filed Apr. 24, 2007, is incorporated into the present application by literature reference. With regard to the abovementioned teachings, numerous changes and deviations from the present invention are possible.
It can therefore be assumed that the invention, within the scope of the appended claims, can be performed differently from the way described specifically herein.

The invention claimed is:

1. A process for starting-up a heterogeneously catalyzed partial gas phase oxidation of acrolein to acrylic acid or of methacrolein to methacrylic acid in a fixed catalyst bed which is disposed in a tube bundle reactor in the reaction tubes of a vertical bundle of reaction tubes surrounded by a reactor jacket, both ends of the individual reaction tubes being open and the upper end of each reaction tube ending sealed into a passage orifice of an upper tube plate sealed at the top into the reactor jacket and the lower end ending sealed into a passage orifice of a lower tube plate sealed at the bottom into the reactor jacket, the exterior of the reaction tubes, the upper and the lower tube plate and the reactor jacket together delimiting the reaction tube surrounding space, and each of the two tube plates being spanned by a reactor hood having at least one orifice, in which, in order to begin the startup, a reaction gas entry mixture comprising $\geq 3\%$ by volume of acrolein or methacrolein and also molecular oxygen is fed to the reaction tubes of the tube bundle reactor via the at least one orifice, referred to hereinafter as E, in one of the two reactor hoods, and the product gas mixture which results through partial gas phase oxidation of acrolein or methacrolein to acrylic acid or methacrylic acid in the course of passage through the fixed catalyst bed disposed in the reaction tubes and comprises acrylic acid or methacrylic acid is removed via the at least one orifice of the other reactor hood, while, on the jacket side of the tube bundle reactor, at least one liquid heat exchange medium is conducted around the reaction tubes such that each of the two surfaces of the two tube plates facing one another are wetted by liquid heat exchange medium and the at least one liquid heat exchange medium is conducted into the reaction tube surrounding space with the temperature $T_H^{in}$ and is conducted out of the reaction tube surrounding space again with the temperature $T_H^{out}$, wherein, at the time at which, in order to begin the startup, the reaction gas entry mixture comprising $\geq 3\%$ by volume of acrolein or methacrolein enters the reactor hood through the at least one orifice E, the temperature $T_H^{in}$ of the at least one liquid heat exchange medium which wets the tube plate spanned by the reactor hood having the at least one orifice E, referred to hereinafter as reactor plate E, is at least 290° C., the reaction gas entry mixture which enters the at least one orifice E has a temperature of $\leq 285°$ C., and the temperature of the surface of the reactor plate E facing the reactor hood having the at least one orifice E, referred to hereinafter as reactor plate surface E, has a value of $\leq 285°$ C.

2. The process according to claim 1, wherein the temperature $T_H^{in}$ of the at least one liquid heat exchange medium which wets the reactor plate E is at least 295° C.

3. The process according to claim 1, wherein the temperature $T_H^{in}$ of the at least one liquid heat exchange medium which wets the reactor plate E is at least 300° C.

4. The process according to any of claims 1 to 3, wherein the reaction gas entry mixture entering the at least one orifice E has a temperature of $\leq 280°$ C.

5. The process according to any of claims 1 to 3, wherein the reaction gas entry mixture entering the at least one orifice E has a temperature of $\leq 270°$ C.

6. The process according to claims 1 to 3, wherein the temperature of the reactor plate surface E has a value of $\leq 280°$ C.

7. The process according to claims 1 to 3, wherein the temperature of the reactor plate surface E has a value of $\leq 275°$ C.

8. The process according to any of claims 1 to 3, wherein the reaction gas entry mixture comprises at least 4% by volume of acrolein or methacrolein.

9. The process according to any of claims 1 to 3, wherein the reaction gas entry mixture comprises at least 5% by volume of acrolein or methacrolein.

10. The process according to any of claims 1 to 3, wherein the molar ratio of $O_2$: (acrolein or methacrolein) in the reaction gas entry mixture is $\geq 0.5$.

11. The process according to any of claims 1 to 3, wherein the loading of the fixed catalyst bed with acrolein or methacrolein is $\geq 101$ (STP)(l·h).

12. The process according to any of claims 1 to 3, wherein the reactor plate E has a cross-sectional area of from 3 m² to 80 m².

13. The process according to any of claims 1 to 3, wherein the reactor plate E has a reactor plate thickness of from 5 to 40 cm.

14. The process according to any of claims 1 to 3, wherein the reactor plate E is manufactured from steel.

15. The process according to any of claims 1 to 3, wherein the at least one heat exchange medium is a salt melt or a heat carrier oil.

16. The process according to any of claims 1 to 3, wherein the reactor hood which spans the reactor plate E, on its side facing the reactor plate E, is plated with stainless steel or with zinc silicate primer.

* * * * *